United States Patent
Lee et al.

(10) Patent No.: US 10,010,400 B2
(45) Date of Patent: Jul. 3, 2018

(54) DEVICES AND METHODS FOR LOCAL DELIVERY OF DRUG TO UPPER URINARY TRACT

(71) Applicant: TARIS Biomedical LLC, Lexington, MA (US)

(72) Inventors: Heejin Lee, Bedford, MA (US); Cheryl Larrivee-Elkins, Framingham, MA (US); Hong Linh Ho Duc, Weston, MA (US); Colin Mixter, Exeter, NH (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 15/085,179

(22) Filed: Mar. 30, 2016

(65) Prior Publication Data
US 2016/0287369 A1    Oct. 6, 2016

Related U.S. Application Data

(60) Provisional application No. 62/140,077, filed on Mar. 30, 2015.

(51) Int. Cl.
*A61F 2/94*    (2013.01)
*A61K 9/22*    (2006.01)
(Continued)

(52) U.S. Cl.
CPC .................. *A61F 2/04* (2013.01); *A61F 2/94* (2013.01); *A61K 31/7068* (2013.01);
(Continued)

(58) Field of Classification Search
CPC ............ A61B 5/6862; A61B 17/00234; A61B 1/307; A61B 5/20; A61F 2002/048; A61F 2250/0068; A61F 2/04; A61F 2/94
See application file for complete search history.

(56) References Cited

U.S. PATENT DOCUMENTS

| 4,871,542 A | 10/1989 | Vilhardt |
| 6,287,608 B1 | 9/2001 | Levin et al. |

(Continued)

FOREIGN PATENT DOCUMENTS

| WO | 1990/13332 A1 | 11/1990 |
| WO | 2012/019155 A1 | 2/2012 |

(Continued)

OTHER PUBLICATIONS

Krambeck, Amy E. et al., "A Novel Drug Eluting Ureteral Stent: A Prospective, Randomized, Multicenter Clinical Trial to Evaluate the Safety and Effectiveness of a Ketorolac Loaded Ureteral Stent," 2010 American Urological Association Education and Research, Inc., vol. 183, 1037-1043, Mar. 2010.
(Continued)

*Primary Examiner* — Ann Schillinger
(74) *Attorney, Agent, or Firm* — Eversheds Sutherland (US) LLP

(57) ABSTRACT

Drug delivery devices include a flexible elongate body having a bladder end portion, a kidney end portion, and a drug lumen extending therebetween; and a drug reservoir which is located at the bladder end portion, contains a drug, and is defined at least in part by a semi-permeable wall. Methods include inserting the device into the ureter of a patient and permitting water in the bladder to diffuse through the semi-permeable wall to create an osmotic pressure to pump the drug through the drug lumen and out of the device at the kidney end portion and into the renal pelvis.

30 Claims, 14 Drawing Sheets

(51) Int. Cl.
*A61M 31/00* (2006.01)
*A61F 2/04* (2013.01)
*A61K 31/7068* (2006.01)
*A61M 27/00* (2006.01)

(52) U.S. Cl.
CPC ........ *A61M 27/008* (2013.01); *A61M 31/002* (2013.01); *A61F 2002/048* (2013.01); *A61F 2250/0068* (2013.01)

(56) References Cited

U.S. PATENT DOCUMENTS

| | | | |
|---|---|---|---|
| 6,368,356 B1 | 4/2002 | Zhong et al. | |
| 6,532,387 B1 | 3/2003 | Marchitto et al. | |
| 6,638,263 B1 | 10/2003 | Theeuwes et al. | |
| 6,656,162 B2 | 12/2003 | Santini, Jr. et al. | |
| 6,726,920 B1 | 4/2004 | Theeuwes et al. | |
| 6,824,532 B2 | 11/2004 | Gillis et al. | |
| 6,899,731 B2 | 5/2005 | Li et al. | |
| 6,921,390 B2 | 7/2005 | Bucay-Couto et al. | |
| 6,949,125 B2 | 9/2005 | Robertson | |
| 7,241,273 B2 | 7/2007 | Maguire et al. | |
| 7,288,084 B2 | 10/2007 | Li | |
| 7,445,642 B2 * | 11/2008 | Amos | A61M 27/008 604/8 |
| 7,749,203 B2 | 7/2010 | Bucay-Couto et al. | |
| 7,857,804 B2 | 12/2010 | McCaffrey et al. | |
| 7,862,552 B2 | 1/2011 | McIntyre et al. | |
| 7,955,372 B2 | 6/2011 | Butterwick et al. | |
| 8,048,168 B2 | 11/2011 | Dillinger | |
| 8,048,171 B2 * | 11/2011 | Li | A61M 27/002 604/8 |
| 8,167,836 B2 | 5/2012 | Lee et al. | |
| 8,182,464 B2 | 5/2012 | Lee et al. | |
| 8,343,516 B2 | 1/2013 | Daniel et al. | |
| 8,414,656 B2 | 4/2013 | Davoudi et al. | |
| 8,512,272 B2 | 8/2013 | Ostrovsky et al. | |
| 8,597,367 B2 | 12/2013 | Dillinger | |
| 8,652,200 B2 | 2/2014 | Weber | |
| 8,685,427 B2 | 4/2014 | Li et al. | |
| 8,691,264 B2 | 4/2014 | Li et al. | |
| 8,721,711 B2 | 5/2014 | Hanson | |
| 8,728,169 B2 | 5/2014 | Li | |
| 8,740,989 B2 | 6/2014 | Davoudi et al. | |
| 8,840,678 B2 | 9/2014 | Sudhir et al. | |
| 8,940,056 B2 | 1/2015 | Li | |
| 8,946,209 B2 | 2/2015 | Brookoff | |
| 8,974,368 B2 | 3/2015 | Dinh | |
| 9,066,823 B2 | 6/2015 | Ostrovsky et al. | |
| 9,101,685 B2 | 8/2015 | Li et al. | |
| 9,108,028 B2 | 8/2015 | Consigny et al. | |
| 9,216,239 B2 | 12/2015 | Rubin | |
| 9,233,238 B2 | 1/2016 | Buysman et al. | |
| 2002/0188246 A1 | 12/2002 | Hayner et al. | |
| 2005/0169969 A1 | 8/2005 | Li et al. | |
| 2006/0052757 A1 | 3/2006 | Fischer, Jr. et al. | |
| 2007/0178138 A1 | 8/2007 | Pal et al. | |
| 2008/0004578 A1 | 1/2008 | Hixon et al. | |
| 2008/0044452 A1 | 2/2008 | Carey | |
| 2008/0234659 A1 | 9/2008 | Cheng et al. | |
| 2008/0261960 A1 * | 10/2008 | Brown | A61K 8/4986 514/226.2 |
| 2009/0117053 A1 | 5/2009 | Li | |
| 2009/0130017 A1 | 5/2009 | Allen et al. | |
| 2009/0142413 A1 | 6/2009 | Allen et al. | |
| 2009/0171465 A1 | 7/2009 | Bucay-Couto et al. | |
| 2009/0187254 A1 | 7/2009 | Deal et al. | |
| 2009/0247992 A1 | 10/2009 | Shalon et al. | |
| 2009/0292237 A1 | 11/2009 | Overstreet et al. | |
| 2009/0312833 A1 | 12/2009 | Tittelbach et al. | |
| 2010/0145467 A1 | 6/2010 | Davoudi et al. | |
| 2010/0331770 A1 | 12/2010 | Lee et al. | |
| 2011/0060309 A1 | 3/2011 | Lee et al. | |
| 2011/0152839 A1 | 6/2011 | Cima et al. | |
| 2011/0202036 A1 | 8/2011 | Boyko et al. | |
| 2011/0218488 A1 | 9/2011 | Boyko et al. | |
| 2012/0035410 A1 | 2/2012 | Borgos et al. | |
| 2012/0063997 A1 | 3/2012 | Hunter et al. | |
| 2012/0141587 A1 | 6/2012 | Yoo et al. | |
| 2012/0195939 A1 | 8/2012 | Nadal-Ginard | |
| 2013/0131637 A1 | 5/2013 | DiCesare et al. | |
| 2013/0158675 A1 * | 6/2013 | Hutchins, II | A61M 25/0017 623/23.66 |
| 2013/0178824 A1 | 7/2013 | Buelna | |
| 2013/0280316 A1 | 10/2013 | Pal et al. | |
| 2013/0309304 A1 | 11/2013 | Nadal-Ginard | |
| 2014/0025037 A1 | 1/2014 | Elins et al. | |
| 2014/0088347 A1 | 3/2014 | Frigstad et al. | |
| 2014/0093473 A1 * | 4/2014 | Hauser | C07K 5/101 424/78.17 |
| 2014/0142721 A1 | 5/2014 | Robertson et al. | |
| 2014/0214175 A1 | 7/2014 | Barron et al. | |
| 2014/0221964 A1 | 8/2014 | Xiao et al. | |
| 2014/0242144 A1 | 8/2014 | Sudhir et al. | |
| 2014/0358245 A1 | 12/2014 | Harrah et al. | |
| 2015/0005893 A1 | 1/2015 | Harrah et al. | |
| 2015/0088150 A1 | 3/2015 | Lee et al. | |
| 2015/0174293 A1 | 6/2015 | Dinh | |
| 2015/0250581 A1 | 9/2015 | Ostrovsky et al. | |
| 2015/0343118 A1 | 12/2015 | Li et al. | |
| 2015/0366974 A1 | 12/2015 | Holzer et al. | |

FOREIGN PATENT DOCUMENTS

| | | |
|---|---|---|
| WO | 2012/154946 A1 | 11/2012 |
| WO | 2013/011504 A1 | 1/2013 |
| WO | 2014/071387 A1 | 5/2014 |
| WO | 2015/026813 A1 | 2/2015 |

OTHER PUBLICATIONS

Taylor, William N. et al., "Minimally Invasive Ureteral Stent Retrieval," The Journal of Urology, vol. 168, 2020-2023, Nov. 2002.

International Search Report and Written Opinion for International Application No. PCT/US2016/024935, dated Jul. 5, 2016 (15 pages).

\* cited by examiner

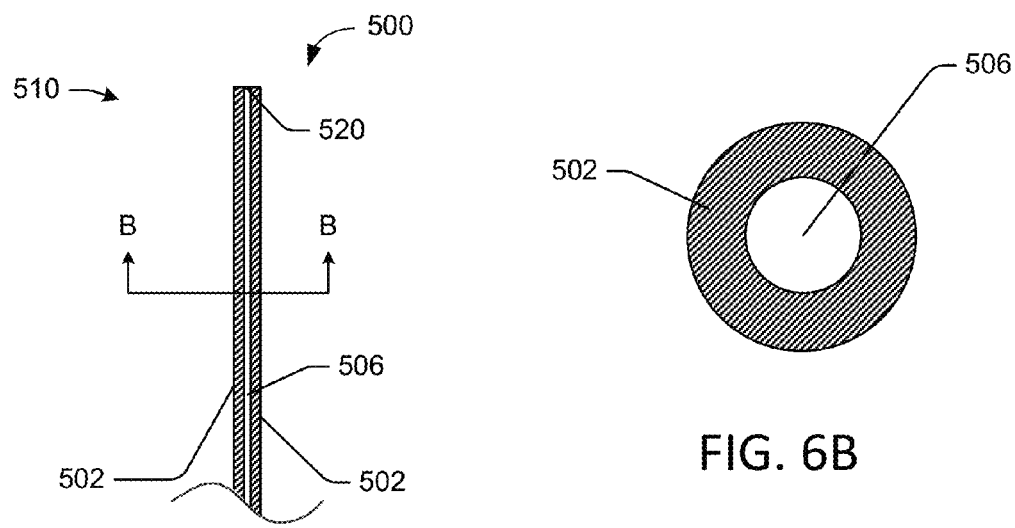
FIG. 6B
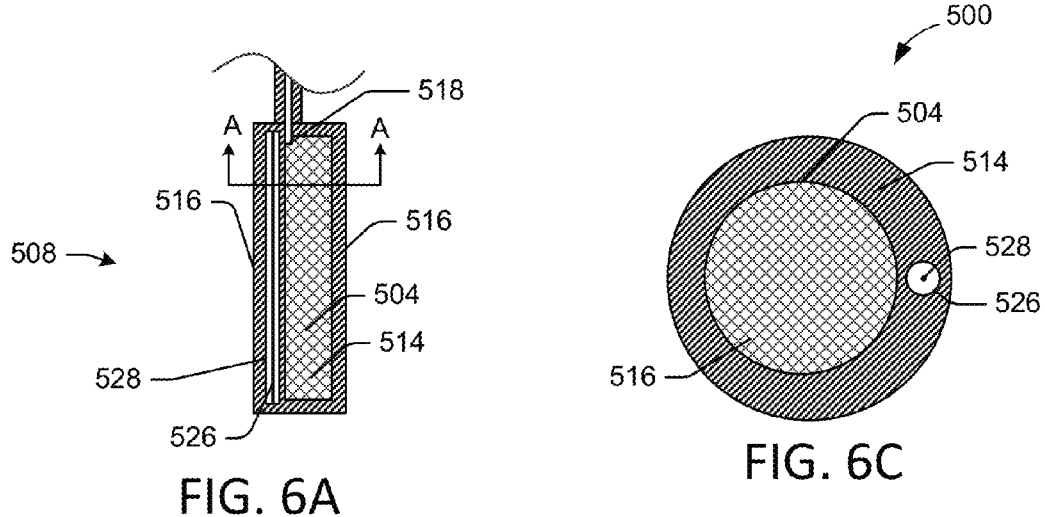
FIG. 6A
FIG. 6C

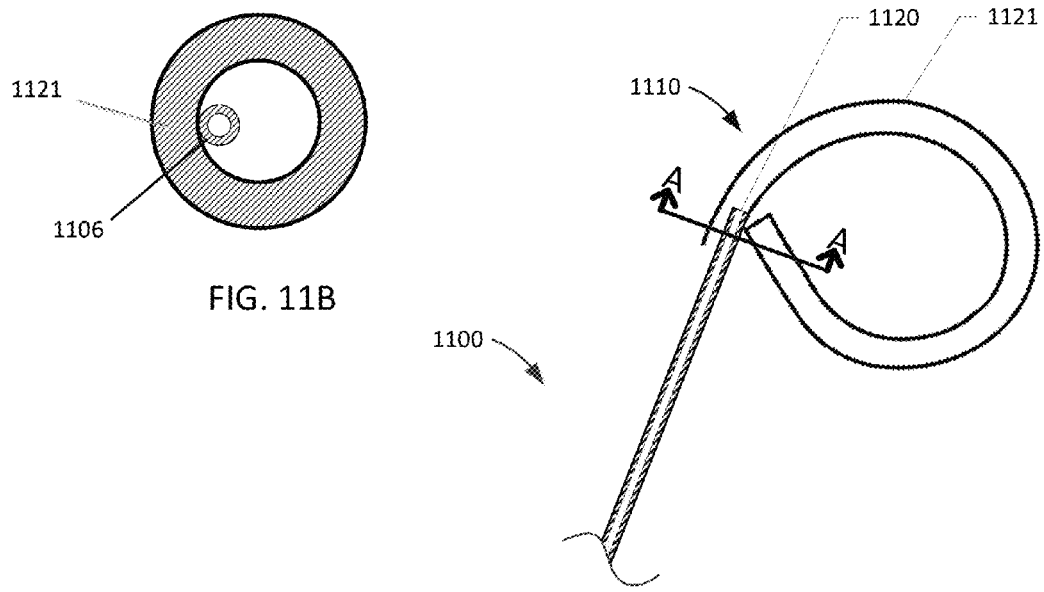
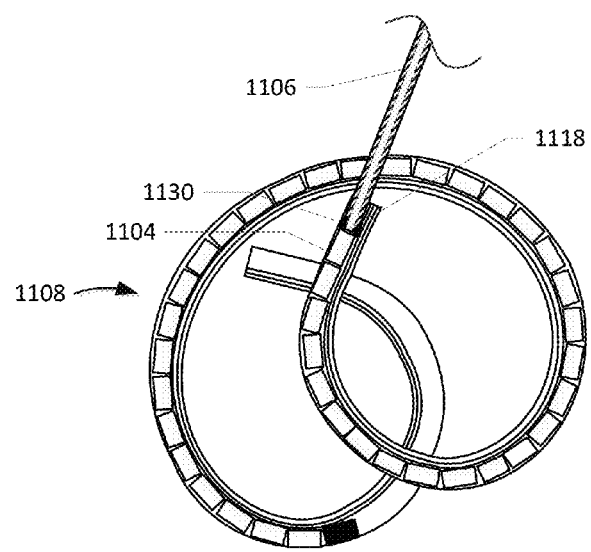
FIG. 11B
FIG. 11A

DEVICES AND METHODS FOR LOCAL DELIVERY OF DRUG TO UPPER URINARY TRACT

CROSS-REFERENCE TO RELATED APPLICATIONS

This application claims priority to U.S. Provisional Application No. 62/140,077, filed Mar. 30, 2015, the entire content of which is incorporated by reference herein.

TECHNICAL FIELD

The present disclosure is generally in the field of drug delivery devices and methods, and more particularly to devices and methods for targeted delivery of drug to a selected region of the body, including but not limited to the renal pelvis, ureters, and/or urinary bladder.

BACKGROUND

Current approaches for the delivery of drug to the upper urinary tract, such as to treat upper urinary tract infections (UTIs), upper tract urothelial carcinoma (UTUC), and related complications, are unsatisfactory. For example, topical urinary tract instillation has been used to treat UTUC; however, such instillations suffer the drawback of providing only a relatively short and insufficient duration of drug exposure, or dwell time (Audenet et al., "Upper Urinary Tract Instillations in the Treatment of Urothelial Carcinomas: A Review of Technical Constraints and Outcome" *World J. Urol.* 31(1):45-52 (February 2013)). UTIs are currently treated using systemic (e.g., oral) antibiotic therapy, requiring large doses of drug for multiple days or weeks, which undesirably increases the risk of side effects including nephrotoxicity and/or the development of a superinfection and drug resistance.

Efforts have been proposed to improve drug instillation dwell times in the treatment of UTUC by instilling the drugs with hydrogel polymers having reverse thermal gelation properties (liquid state at cold temperatures and solid state at body temperature). However, these hydrogel polymers have been found to still have relatively short retention potential and therefore, similar to conventional instillation treatments, are believed to be incapable of delivering drug to a treatment area for a sufficient period (e.g., more than a day) to provide a therapeutic effect.

Ureteral drug delivery stents are known. For example, some ureteral stents have been made of a drug-impregnated polymer. However, drug release from such matrix material release systems has been generally unsatisfactory due to the relatively low drug payload that such systems are able to contain and deliver. Furthermore, release of drug is limited by diffusion from and/or degradation of the polymer matrix, which limits the drug release rates that can be achieved. Mechanical requirements of the matrix-drug composition further limit the total amount of drug payload that can devices can contain.

Another ureteral stent-type device is disclosed in U.S. Pat. No. 9,259,517. The device requires a balloon portion, which resides within the bladder and which must be filled with a drug solution after the device is deployed in the bladder. This feature unfortunately complicates the process of using the device. It also requires an undesirably large and potentially intolerable (or at least highly uncomfortable, to the patient) drug reservoir reside in the bladder during the period of drug release, due to the large volume needed for the inflated balloon to contain both the drug and all of the liquid vehicle needed for releasing the drug.

It therefore would be desirable to provide new and improved methods and devices for controlled delivery of drug to the renal pelvis area in effective amounts for extended periods. It would be desirable for such drug delivery devices and methods to be easily inserted into and removed from a patient's ureter, preferably without requiring an additional step to load a liquid vehicle into (or remove the liquid vehicle from) the device's drug reservoir after the device has been inserted into the patient's bladder.

SUMMARY

In one aspect, drug delivery devices are provided, which may be used for placement within a ureter of a patient. The device includes a flexible elongate body having a bladder end portion, a kidney end portion, and a drug lumen extending between the bladder end portion and the kidney end portion; a drug reservoir which is located in the first end portion, contains a drug, and is defined at least in part by a semi-permeable wall; wherein the drug lumen has a first end opening into the drug reservoir and a second opening at the kidney end portion of the flexible elongate body, wherein the device is configured, in use, to permit water to enter the drug reservoir through the semi-permeable wall to create an osmotic pressure to pump the drug from the drug reservoir through the drug lumen and out of the device through the second end opening.

In another aspect, methods of treatment and methods of administering a drug to a patient in need thereof are provided. In one embodiment, the method includes inserting a drug delivery device including a flexible elongate body having a bladder end portion, a kidney end portion, and a drug lumen extending between the bladder end portion and the kidney end portion, through the patient's urethra and bladder and into at least one of the patient's ureters, such that the bladder end portion of the device is located within the bladder of the patient and the kidney end portion of the device is located within a kidney of the patient, wherein the bladder end portion includes a drug reservoir that is defined at least in part by a semi-permeable wall and contains a drug; and permitting water in the bladder to diffuse through the semi-permeable wall of the device to create an osmotic pressure to pump the drug from the drug reservoir through the drug lumen and out of the device through an opening at the kidney end portion of the device and into the renal pelvis. The methods provide for local and continuous drug delivery to the renal pelvis over an extended period.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. In some figures, the relative size of certain elements and/or components exaggerated for ease of illustration. Throughout this disclosure, depending on the context, singular and plural terminology may be used interchangeably.

FIG. 6A is a cross-sectional view of a drug delivery device in a deployment shape in accordance with an embodiment of the present disclosure.

FIG. 6B is a cross-sectional view proximate to the kidney end portion taken along line B-B of the drug delivery device in FIG. 6A.

FIG. 6C is a cross-sectional view of the bladder end portion taken along line A-A of the drug delivery device in FIG. 6A.

FIG. 11A is a cross-sectional view of a drug delivery device in a retention shape in accordance with an embodiment of the present disclosure.

FIG. 11B is a cross-sectional view of the kidney end portion taken along line A-A of the drug delivery device in FIG. 11A.

DETAILED DESCRIPTION

Figure 1A:
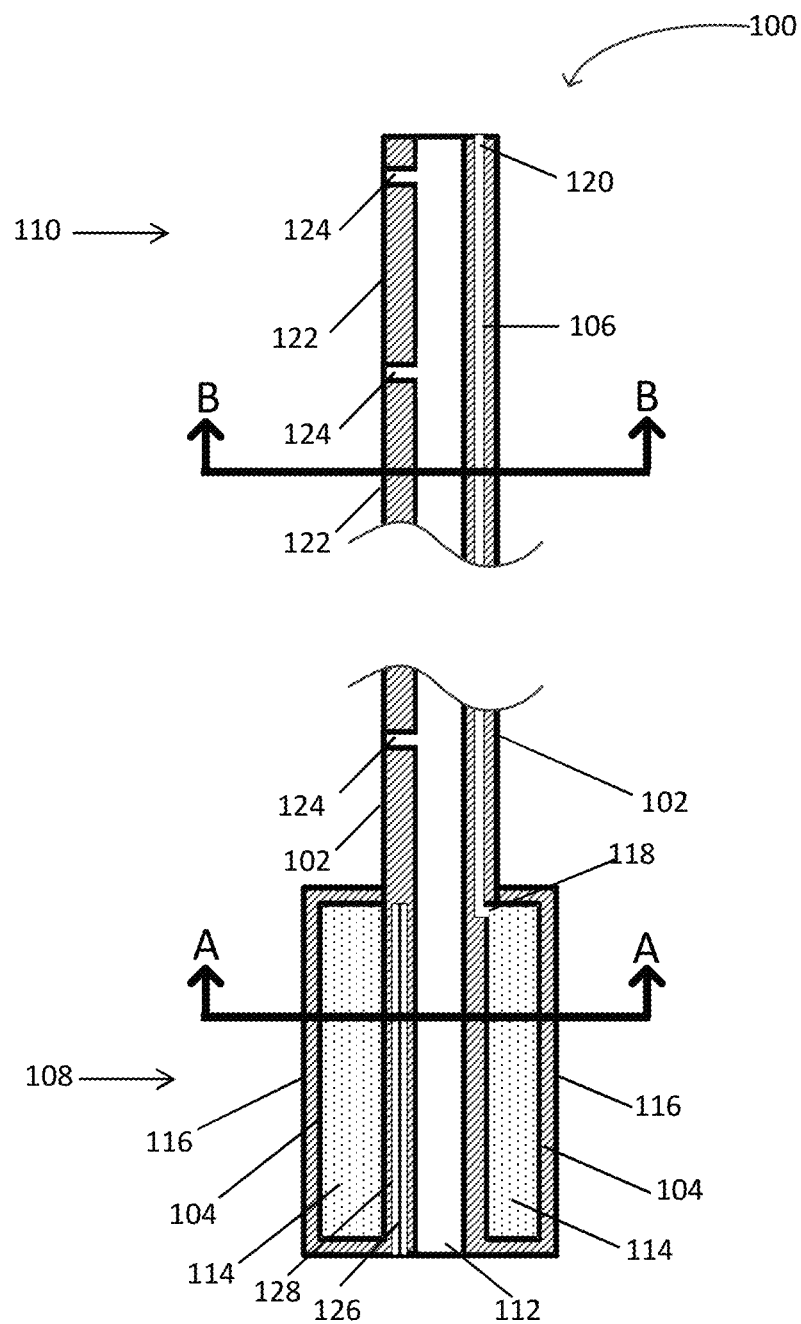
FIG. 1A is a cross-sectional view of a drug delivery stent device in a deployment shape in accordance with an embodiment of the present disclosure.

Improved devices and methods have been developed for controlled, extended local delivery of a drug to the upper urinary tract of a patient. The devices and methods advantageously include a bladder-residing drug reservoir that is configured to operate as an osmotic pump to push drug from the reservoir through a flexible elongate luminal body (e.g., a capillary tube) extending from the drug reservoir through a ureter for release of the drug into the renal pelvis/upper urinary tract. The devices and methods can be used to treat the tissues of or in the renal pelvis, renal calyces, and/or ureters.

The devices may be configured to include a ureteral stent or may operate in conjunction with a conventional ureteral stent. In one embodiment, a kit of parts is provided, which includes a first part which comprises a ureteral stent having a bladder-residing end and a kidney-residing end; and a second part which comprises a drug delivery device which comprises a drug reservoir configured for attachment to the ureteral stent at or about the bladder-residing end, wherein the drug reservoir contains a drug and is in fluid communication with a capillary tube having a first end connected to the drug reservoir and an opposed second end positionable at or about the kidney-residing end of the ureteral stent.

In embodiments, the drug delivery devices described herein include a flexible elongate body which has a bladder end portion, an opposed a kidney end portion, and, optionally, a drainage lumen extending therebetween. The device also includes a drug reservoir disposed at the bladder end portion of the flexible elongate body and a drug lumen extending from the drug reservoir to the kidney end portion, such that the device advantageously is configured, in use, to osmotically pump a drug from the drug reservoir, through the drug lumen, and out of the device at the kidney end portion and directly into the renal pelvis of the patient. This configuration advantageously enables the device to store the drug within the bladder end portion in a space efficient manner (e.g., without the need to also contain at one time the entire liquid vehicle needed for delivery of the drug) and also to be able to locally administer drug to directly the renal pelvis. In other words, this device beneficially provides for local and continuous drug delivery to the renal pelvis over an extended period without being limited by the structural parameters of the patient's ureter and kidney.

The devices disclosed herein also advantageously are designed to enable the device to be pre-loaded with the full amount of drug required for a course of therapy prior to insertion of the device into the patient, thereby avoiding the need to subject the patient to additional or more complicated procedures to load or re-load the devices with drug after the device is deployed in vivo (e.g., in the bladder).

The present drug delivery devices also advantageously are able to release drug directly into the renal pelvis without needing to locate the drug reservoir in the kidney. This is accomplished by having the drug reservoir, with the accompanying volume/space requirement for the drug payload located in the bladder and providing a means for pumping the drug to the kidney in a controlled manner. In this way, it beneficially is not required for the drug reservoir to have a diameter small enough to pass into/through a ureter.

The Drug Delivery Devices

In certain embodiments, the drug delivery device includes a flexible elongate body which has a bladder end portion, a kidney end portion, and a drug lumen extending between the bladder end portion and the kidney end portion. The device also includes a drug reservoir that contains a drug and is located at the bladder end portion. The drug lumen has a first end opening into the drug reservoir and a second end opening at the kidney end portion of the flexible elongate body. The drug reservoir is defined at least in part by a semi-permeable wall, such that the device, during use, can permit water (urine) to enter the drug reservoir through the semi-permeable wall and create an osmotic pressure in the reservoir. In particular embodiments, the water entering the drug reservoir solubilize the drug and excipients stored therein (e.g., which may be in tablet or other solid form), wherein the solubilized drug and excipients cannot diffuse through the semi-permeable wall (or other wall portions of the device), which creates the osmotic pressure. The osmotic pressure is relieved by driving the drug (liquid, solution, or suspension) from the drug reservoir through the drug lumen and out of the device through the second end opening. The drug delivery device can be inserted inside the ureter of patient, such that the drug delivery device acts as an osmotic pump to deliver drug directly to the renal pelvis of the patient.

In some embodiments, the device is further configured to release drug from the bladder end portion, in addition to the kidney end portion. In one embodiment, the drug delivery device includes a second drug reservoir containing a second drug (which may be the same as or different from the drug delivered from the second end portion) and the second drug is released from the bladder end portion of the device. The second drug may be released by diffusion or by osmotic pressure, for example. In one case, the second reservoir includes a release aperture for releasing solubilized drug after water/urine has permeated through a semi-permeable wall member defining at least part of the second drug reservoir.

The drug delivery devices may have or be configured for use with a ureteral stent. For example, the flexible elongate body may at least partially form a ureteral stent. That is, the flexible elongate body may be configured for insertion into the ureter to maintain the passageway open and may include a drainage lumen to allow the flow of urine between the kidney and the bladder. In other embodiments, the drug delivery device is configured for use in conjunction with a pre-existing ureteral stent. For example, the flexible elongate body may have an outer diameter small enough to be inserted into a conventional ureteral stent and still allow for drainage of fluid from the kidney to the bladder of the patient through the ureteral stent.

The phrase "drug delivery stent device" is used herein to refer to devices in which the flexible elongate body at least partially functions as a ureteral stent. One embodiment of the drug delivery stent device is shown in FIGS. 1A-1D. The drug delivery stent includes a flexible elongate body 102, which has a bladder end portion 108, a kidney end portion 110, and a drainage lumen 112 that extends between the bladder end portion 108 and the kidney end portion 110. As used herein, the phrase "extending between" when used to describe the location of the drainage lumen with respect to the bladder and kidney end portions of the flexible elongate body includes embodiments in which the drainage lumen extends into and/or through one or both of the bladder end and kidney end portions. The open ends of the drainage lumen may be located at or near the ends of the elongate body.

In particular, in this embodiment, the drainage lumen 112 has opposed openings at the ends of the two end portions 108, 110. The flexible elongate body 102 includes a sidewall 122 having multiple side drainage holes 124 in fluid communication with the drainage lumen 112. The bladder end portion 108 has a drug reservoir 104, which contains at least one drug 114. The drug reservoir 104 is defined at least in part by a semi-permeable wall 116. The semi-permeable wall 116 is water permeable, to permit water to diffuse into the reservoir 104 and to contact the drug 114 therein. The device 100 further includes a drug lumen 106 that has a first end opening 118 into (i.e., in fluid communication with) the drug reservoir 104 and a second end opening 120 at the end of the kidney end portion 110 of the flexible elongate body 102. As shown in FIG. 1B, the drug lumen 106 is separate from and runs substantially parallel to the drainage lumen 112. As can be seen in FIG. 1C, the drug reservoir 104 has a substantially annular shape and surrounds the drainage lumen 112. In certain embodiments, the drug 114 is in a form that substantially fills the annular-shaped drug reservoir 104. For example, the drug 114 may be in the form of a solid powder or one or more tablets or other solid drug units, which can be sized and positioned to fit in the reservoir. The annular shape of the drug reservoir in this design advantageously enables to the drug to be uniformly surrounded by the semi-permeable wall, which may aid in providing a more uniform exposure to water that diffuses through the wall, which may, in turn, provide a better dissolution and control of release of the drug over the treatment period.

Figure 1B:
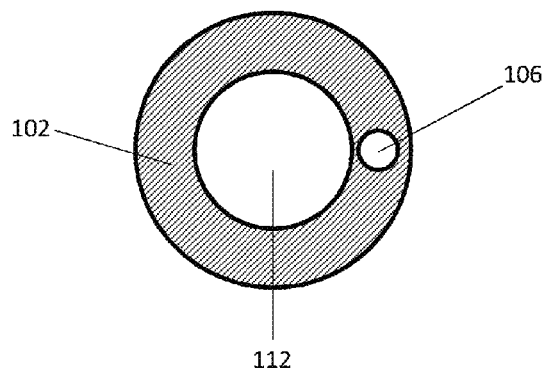
FIG. 1B is a cross-sectional view proximate to the kidney end portion taken along line B-B of the drug delivery stent device in FIG. 1A.
Figure 1C:
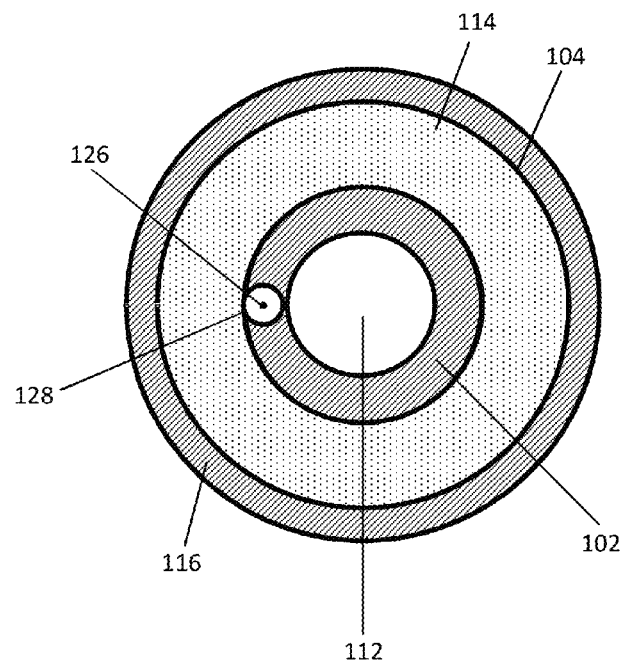
FIG. 1C is a cross-sectional view of the bladder end portion taken along line A-A of the drug delivery stent device in FIG. 1A.
Figure 1D:
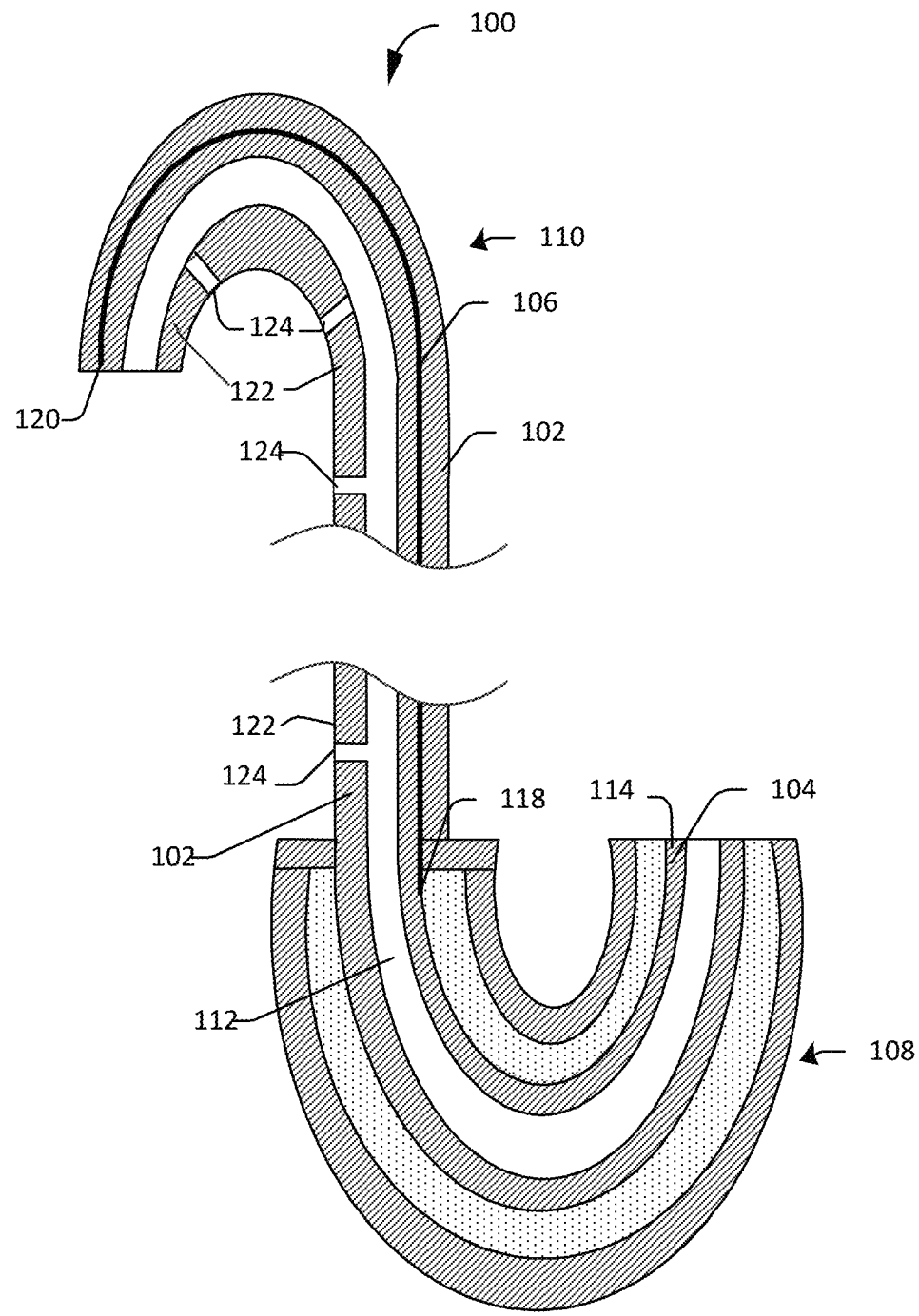
FIG. 1D is a plan view of the drug delivery stent device in FIG. 1A in a retention shape in accordance with an embodiment of the present disclosure.

FIG. 1A shows the drug delivery stent device 100 in a straightened, low-profile shape, which is suitable for passing the device 100 through a cystoscope or other deployment instrument during the procedure for inserting the device 100 into a patient. The straightened shape of the stent device 100 may be maintained by the deployment instrument, while in a working channel of the deployment instrument. FIG. 1D shows the same drug delivery stent device 100 in its coiled, or curved, retention shape. That is, the bladder end portion 108 and the kidney end portion 110 are each in a curved configuration, such that position of the drug delivery stent device 100 is maintained within the patient's ureter. For example, the end portions 108, 110 may be biased in the retention shape, such that they spontaneously return to the coiled shape upon exiting the working channel of the deployment instrument. To achieve such a result, the end portions may be molded of a polymeric material in a shape having an elastic limit, modulus, and/or spring constant selected to impede the end portions of the device from assuming the relatively lower-profile shape once inserted into the ureter. In addition, or in the alternative, one or both end portions may include a shape retention wire to impart such an elastic limit, modulus, and/or spring constant selected to impede the end portions of the device from assuming the relatively lower-profile shape once inserted into the ureter. As shown in FIGS. 1A and 1C, the bladder end portion 108 of the device includes a shape retention wire 126 within a wire lumen 128.

Figure 4B:
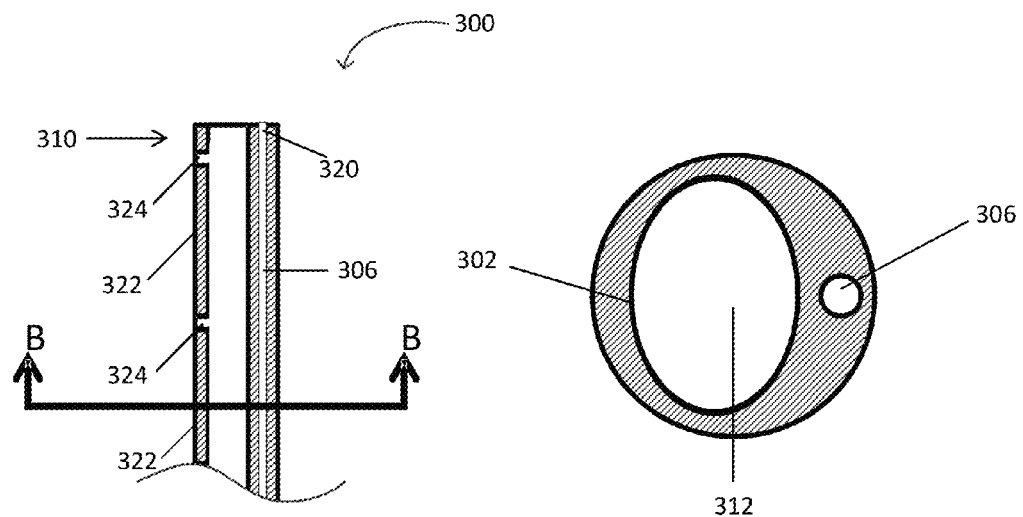
FIG. 4B is a cross-sectional view proximate to the kidney end portion taken along line B-B of the drug delivery stent device in FIG. 4A.
Figure 4A:
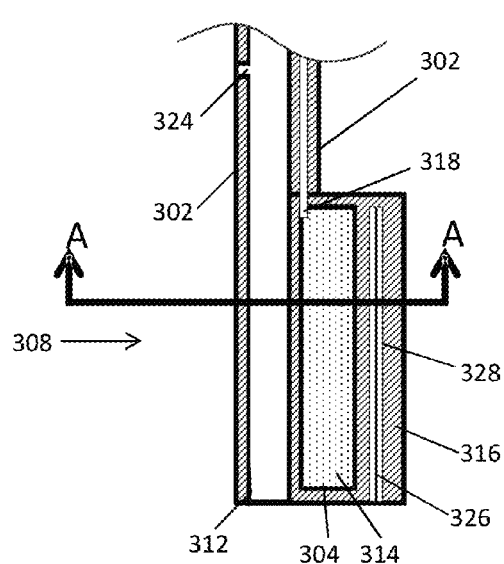
FIG. 4A is a cross-sectional view of a drug delivery stent device in a deployment shape in accordance with another embodiment of the present disclosure.
Figures 4C, 4D:
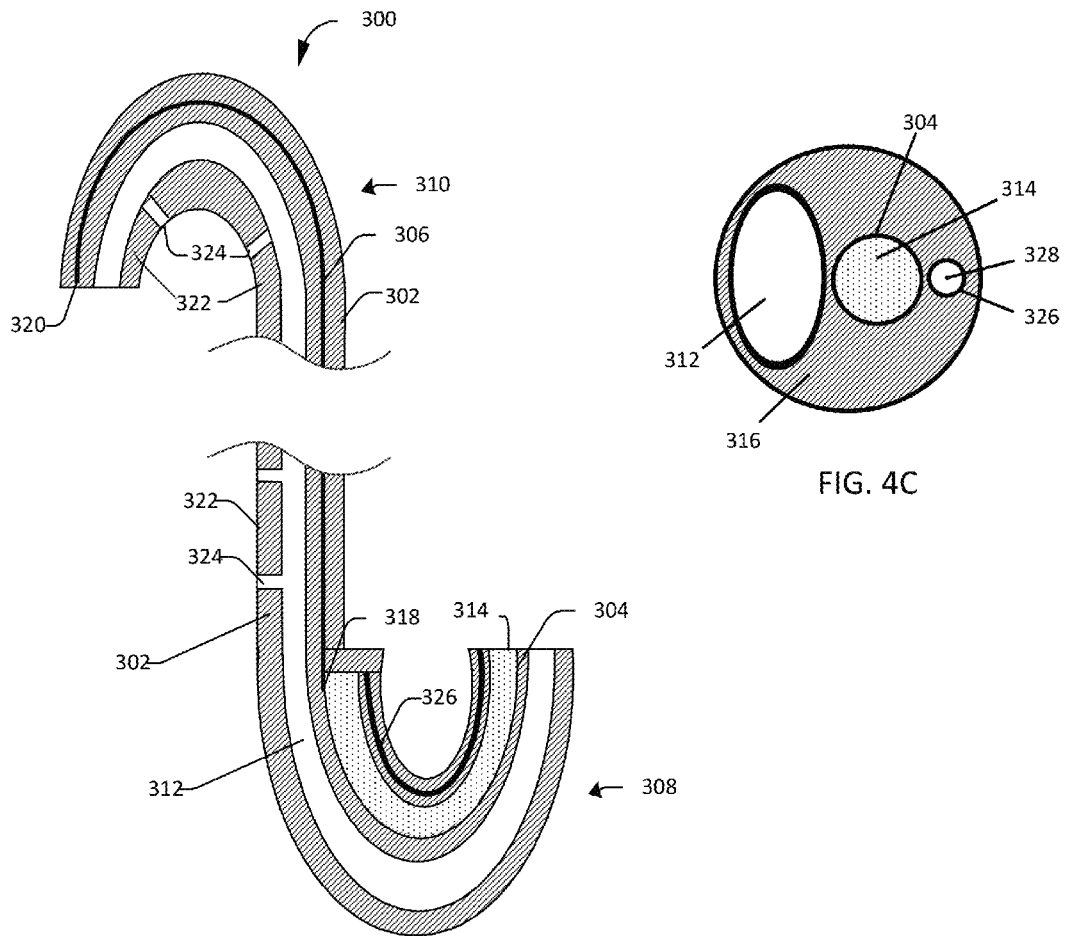
FIG. 4C is a cross-sectional view of the bladder end portion taken along line A-A of the drug delivery stent device in FIG. 4A.
FIG. 4D is a cross-sectional view of the drug delivery stent device in FIG. 4A in a retention shape in accordance with an embodiment of the present disclosure.

Another embodiment of a drug delivery stent device is shown in FIGS. 4A-4D. The drug delivery stent device 300 includes a flexible elongate body 302, which has a bladder end portion 308, a kidney end portion 310, and a drainage lumen 312 that extends between the bladder end portion 308 and the kidney end portion 310. In particular, in this embodiment, the drainage lumen 312 is elliptical in cross-sectional shape and has opposed openings at the ends of the two end portions 308, 310. The flexible elongate body 302 includes a sidewall 322 having multiple side drainage holes 324 in fluid communication with the drainage lumen 312. The bladder end portion 308 has a drug reservoir 304, which contains at least one drug 314. The drug reservoir 304 is defined at least in part by a semi-permeable wall 316. The semi-permeable wall 316 is water permeable, to permit water to diffuse into the reservoir 304 and contact the drug 314 therein. The device 300 further includes a drug lumen 306 that has a first end opening 318 into (i.e., in fluid communication with) the drug reservoir 304 and a second end opening 320 at the end of the kidney end portion 310 of the flexible elongate body 302. As shown in FIG. 4B, the drug lumen 306 is separate from and runs substantially parallel to the drainage lumen 312. As can be seen in FIG. 4C, the drug reservoir 304 is substantially cylindrical and arranged parallel to and to one side of the drainage lumen 312. This non-annular shape of the drug reservoir may be advantageous for easily and efficiently being filled with certain forms of the drug. For example, the cylindrical drug reservoir 304 may be filled with one or more (stacked) cylindrical drug tablets having a diameter substantially equal to the inner diameter of the drug reservoir.

FIG. 4A shows the drug delivery stent device 300 in a straightened, low-profile shape, which is suitable for passing the device 300 through a cystoscope or other deployment instrument during the procedure for inserting the device 300 into a patient. Like with stent device 100 describe above, the straightened shape of the stent device 300 may be maintained by the deployment instrument, while in a working channel of the deployment instrument. FIG. 4D shows the same drug delivery stent device 300 in its coiled, or curved, retention shape. That is, the bladder end portion 308 and the kidney end portion 310 are each in a curved configuration, such that position of the drug delivery stent device 300 is maintained within the patient's ureter. Like end portions 108, 110, the end portions 308, 310 may be biased in the retention shape, such that they spontaneously return to the coiled shape upon exiting the working channel of the deployment instrument. As shown in FIGS. 4A and 4C, the bladder end portion 308 of the device includes a shape retention wire 328 within a wire lumen 326 located within the semi-permeable wall 316.

Figure 5B:
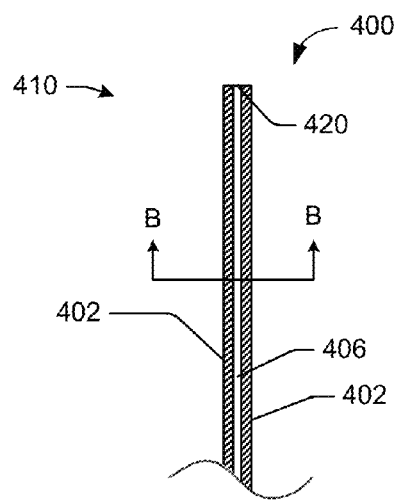
FIG. 5B is a cross-sectional view proximate to the kidney end portion taken along line B-B of the drug delivery device in FIG. 5A.
Figure 5B:
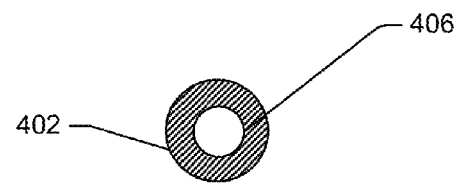
Figure 5A:
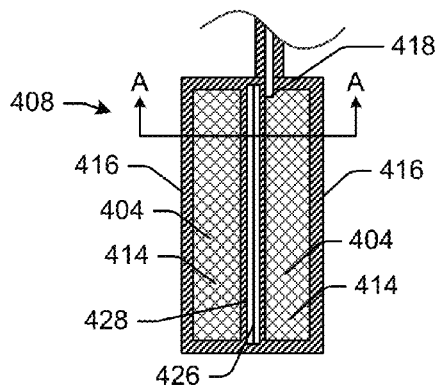
FIG. 5A is a cross-sectional view of a drug delivery device in a deployment shape in accordance with an embodiment of the present disclosure.
Figure 5C:
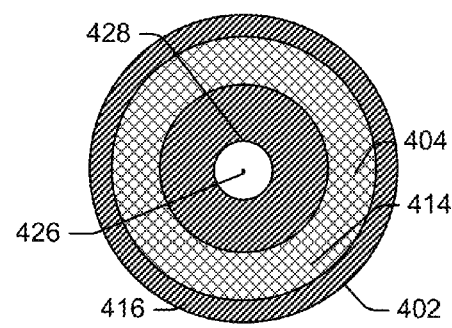
FIG. 5C is a cross-sectional view of the bladder end portion taken along line A-A of the drug delivery device in FIG. 5A.

One embodiment of a drug delivery device that may be combined or used in conjunction with a pre-existing stent is shown in FIGS. 5A-5C. The drug delivery device 400 includes a flexible elongate body 402, which has a bladder end portion 408, a kidney end portion 410. The bladder end portion 408 has a drug reservoir 404, which contains at least one drug 414. The drug reservoir 404 is defined at least in part by a semi-permeable wall 416. The semi-permeable wall 416 is water permeable, to permit water to diffuse into the reservoir 404 and contact the drug 414 therein. The device 400 further includes a drug lumen 406 that has a first end opening 418 into (i.e., in fluid communication with) the drug reservoir 404 and a second end opening 420 at the end of the kidney end portion 410 of the flexible elongate body 402. In certain embodiments, the drug 414 is in the form that substantially fills the annular-shaped drug reservoir 404. For example, the drug 414 may be in the form of a solid powder or one or more tablets or other solid drug units, which can be sized and positioned to fit in the reservoir. The annular shape of the drug reservoir in this design advantageously enables to the drug to be uniformly surrounded by the semi-permeable wall, which may aid in the providing a more uniform exposure to water that diffuses through the wall, which may, in turn, provide a better dissolution and control of release of the drug over the treatment period.

As shown in FIG. 5B, the drug lumen 406 is centered in the flexible elongate body 402. In other embodiments, however, the drug lumen need not be centered in the flexible elongate body, to achieve the desired body strength and flexibility, and support for the drug lumen. As can be seen in FIG. 5C, the drug reservoir 404 has a substantially annular shape and surrounds the drug lumen 406. In certain embodiments, the drug 414 is in the form that substantially fills the annular-shaped drug reservoir 404. For example, the drug 414 may be in the form of a solid powder or one or more tablets or other solid drug units, which can be sized and positioned to fit in the reservoir. As can be seen in FIGS. 5A and 5C, the bladder end portion 408 of the device includes a shape retention wire 426 within a wire lumen 428.

Another embodiment of a drug delivery device that may be combined or used in conjunction with a pre-existing stent is shown in FIGS. 6A-6C. The drug delivery device 500 includes a flexible elongate body 502, which has a bladder end portion 508, and a kidney end portion 510. The bladder end portion 508 has a drug reservoir 504, which contains at least one drug 514. The drug reservoir 504 is defined at least in part by a semi-permeable wall 516. The semi-permeable wall 516 is water permeable, to permit water to diffuse into the reservoir 504 and contact the drug 514 therein. The device 500 further includes a drug lumen 506 that has a first end opening 518 into (i.e., in fluid communication with) the drug reservoir 504 and a second end opening 520 at the end of the kidney end portion 510 of the flexible elongate body 502. FIG. 6A shows the drug delivery device 500 in a straightened, low-profile shape, which is suitable for passing the device 500 through a cystoscope or other deployment instrument during the procedure for inserting the device 500 into a patient or into a traditional ureteral stent. As can be seen in FIG. 5C, the drug reservoir 504 is substantially cylindrical. This non-annular shape of the drug reservoir may be advantageous for easily and efficiently being filled with certain forms of the drug. For example, the cylindrical drug reservoir 504 may be filled with one or more (stacked) cylindrical drug tablets having a diameter substantially equal to the inner diameter of the drug reservoir. As can be seen in FIGS. 6A and 6C, the bladder end portion 508 of the device includes a shape retention wire 526 within a wire lumen 528.

Figure 7A:
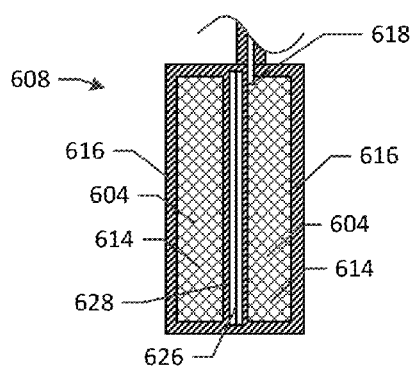
FIG. 7A is a cross-sectional view of a drug delivery device inserted within a ureteral stent in a deployment shape in accordance with an embodiment of the present disclosure.
Figure 7B:
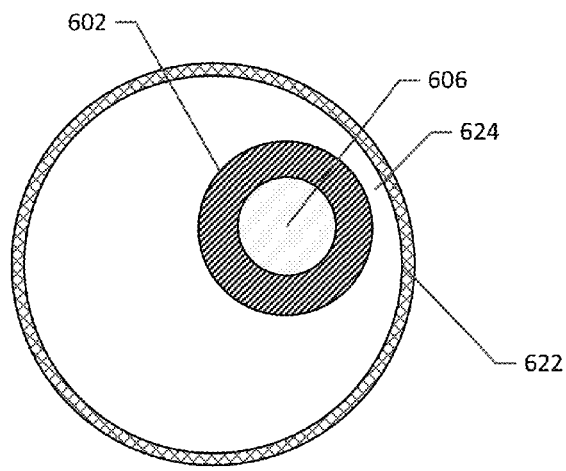
FIG. 7B is a cross-sectional view proximate to the kidney end portion taken along line B-B of the drug delivery device in FIG. 7A.

Another embodiment of the drug delivery device that may be combined or used in conjunction with a pre-existing stent is shown in FIGS. 7A-7B. The drug delivery device 600 includes a flexible elongate body 602, which has a bladder end portion 608, and a kidney end portion 610. The bladder end portion 608 has a drug reservoir 604, which contains at least one drug 614. The drug reservoir 604 is defined at least in part by a semi-permeable wall 616. The semi-permeable wall 616 is water permeable, to permit water to diffuse into the reservoir 604 and contact the drug 614 therein. The device 600 further includes a drug lumen 606 that has a first end opening 618 into (i.e., in fluid communication with) the drug reservoir 604 and a second end opening 620 at the end of the kidney end portion 610 of the flexible elongate body 602. The length of the flexible elongate body 602 of the device 600 can be inserted into a traditional ureteral stent 622, prior to or after deployment of the stent in the ureter. Because the flexible elongate body 602 is substantially smaller in diameter than the inner diameter of the ureteral stent 622, a drainage path 624 is formed between the flexible elongate body 602 and the stent 622, such that urine may drain from the kidney to the bladder through the drainage path 624. FIG. 7A shows the drug delivery device 600 in a straightened, low-profile shape within a traditional ureteral stent 622, which is suitable for passing the device 600 and ureteral stent 622 through a cystoscope or other deployment instrument during the procedure for inserting the device 600 and ureteral stent 622 into a patient, together or separately. As shown in FIG. 7B, the flexible elongate body 602 need not be centered within the stent 622. As can be seen in FIG. 7A, the bladder end portion 608 of the device includes a shape retention wire 626 within a wire lumen 628.

Figure 8:
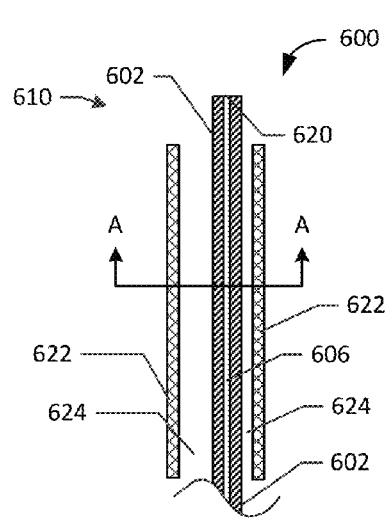
FIG. 8 is a cross-sectional view proximate to the kidney end portion of a drug delivery device positioned adjacent a ureteral stent in accordance with an embodiment of the present disclosure.
Figure 8:
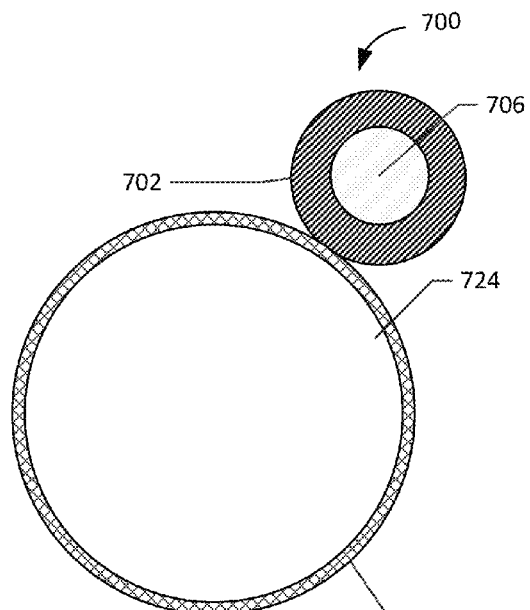

In another embodiment, as shown in FIG. 8, the drug delivery device 700 is configured to be disposed adjacent the outer surface an existing stent 722. In this embodiment, the flexible elongate body 702 defining the drug lumen 706 is attached to the outer surface of the existing stent 722, such that drainage path 724 is wholly maintained.

For example, in embodiments in which the device itself is not configured to function as a urinary stent, the device may be attached by any suitable means to an existing stent. For example, the device may be attached by mechanical or chemical means to an existing stent, during manufacture or by the physician, prior to or after deployment of the stent into the patient. Examples of such attachment means include biocompatible adhesives, clips, spacers, friction fit tabs and mating apertures, snaps, friction fit or adhesively attached hoods, and elastic bands.

Figure 12:
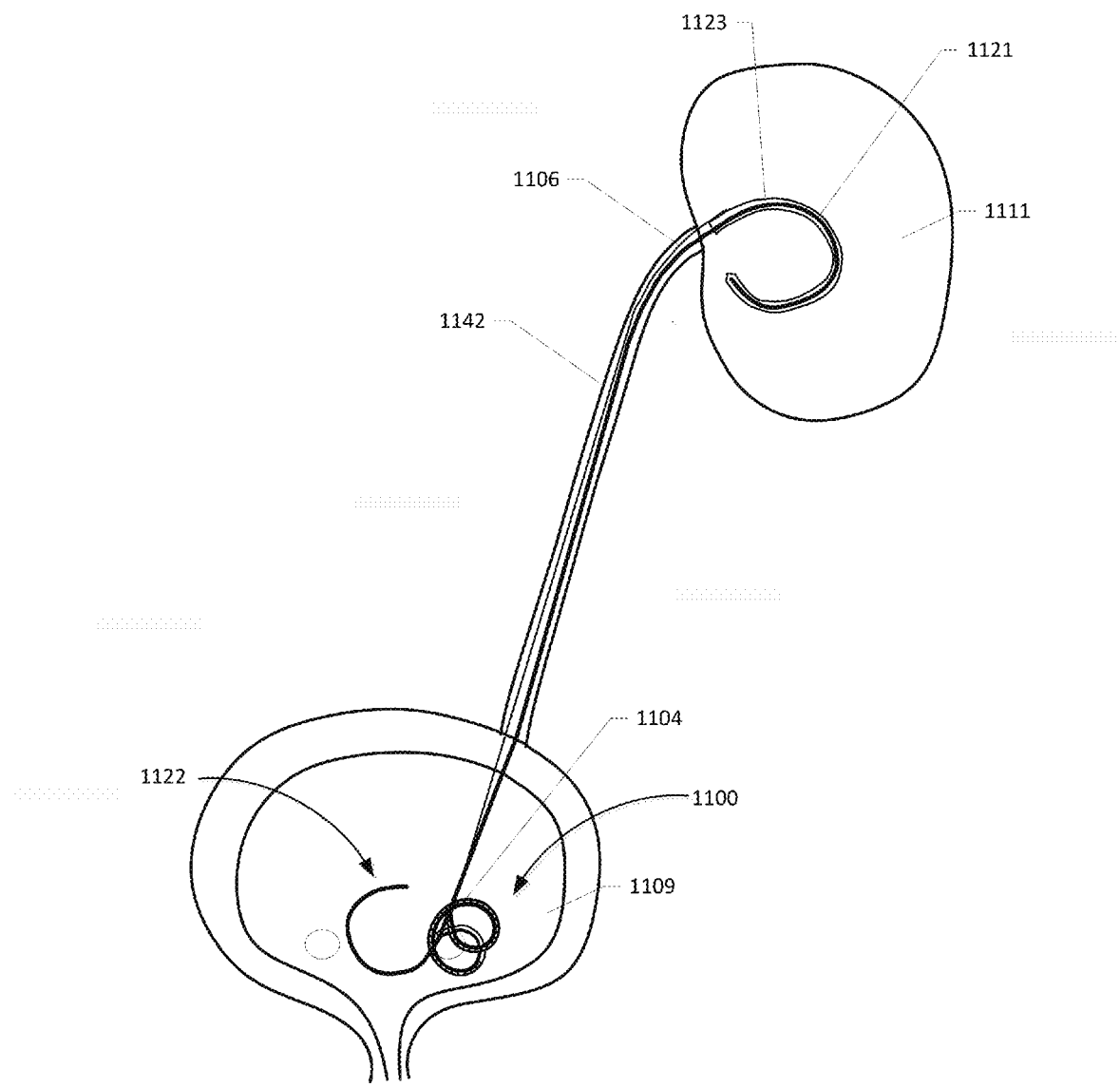
FIG. 12 is a cross-sectional view of a drug delivery device deployed in a patient with an existing stent, in accordance with an embodiment of the present disclosure.

In certain embodiments, as shown in FIGS. 11 and 12, the kidney end portion 1110 of the device 1100 is configured to be attached to the kidney portion 1123 (e.g., renal coil) of an existing stent 1122 by a hood portion 1121. For example, the hood portion 1121 may be a flexible tube configured to fit over the renal coil portion 1123 of the existing stent 1122. The first end opening 1118 of the drug lumen 1106 opens into the drug reservoir 1104 at the bladder end portion 1108 of the device and the second end opening 1120 opens into the hood portion 1121, for release into the renal pelvis. The second end opening 1120 may be disposed at any point along the length of the hood portion 1121, such as near either end of the hood portion or near a midpoint of the hood portion.

For example, the drug lumen 1106 may be formed by a capillary tube or similar structure. In some embodiments, as shown in FIG. 11, the drug lumen 1106 is formed by a capillary tube that is connected at the end of a tubular drug reservoir 1104 by one or more annular spacers 1130 configured to secure the capillary tube within the end of the drug reservoir 1104. In one embodiment, two spacers are disposed in a spaced relationship at an end of the capillary tube and the capillary tube and spacers are slid into the tubular housing of a drug reservoir. A biocompatible adhesive may be applied in the space between the spacers, such as with a needle inserted between the spacer and the drug reservoir tube, to adhere the spacers, capillary tube, and drug reservoir tube. The opposed end of the capillary tube (i.e., the end containing the second end opening) may be configured to attach to an integrated or pre-existing stent, as discussed above. In one embodiment, the opposed end of the capillary tube is connected to a hood portion that is designed to fit over the kidney end of a pre-existing stent. For example, the hood portion may be formed by placing a mandrel within the capillary tube to support and maintain the drug lumen during manufacture and then laminating the capillary tube onto the inner or outer surface of a polymer tube that is sized and shaped to fit over the kidney end portion (e.g., renal coil) of an existing stent. For example, FIG. 11B shows the drug lumen 1106 attached within the tubular hood portion 1121.

Figure 13:
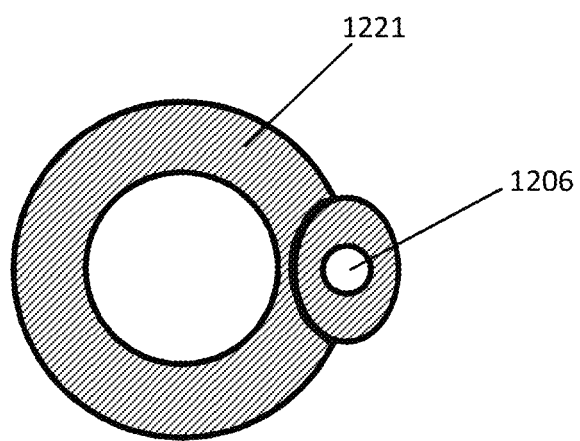
FIG. 13 is a cross-sectional view of the kidney end portion of a drug delivery device, in accordance with an embodiment of the present disclosure.

For example, FIG. 13 shows the drug lumen 1206 attached to the external surface of tubular hood portion 1221. In some embodiments, the end of the hood portion configured to fit over the distal end of the renal coil of the stent may be formed to have a tapered outer surface.

Flexible Elongate Body

The flexible elongate body is sized and shaped to extend through the ureter of a patient from the kidney to the bladder. The flexible elongate body is elastic/flexible such that the body may be easily maneuvered for deployment and positioning within the ureter without undue complications and with minimal discomfort to the patient. When the device is implanted, the kidney end portion is positioned in the kidney, the bladder end portion is positioned in the bladder and, in the drug delivery stent device, the drainage lumen is positioned there between. The drainage lumen facilitates the passage of urine from the kidney to the bladder.

The flexible elongate body is generally made of biocompatible polymeric materials known in the art. In certain embodiments, the biocompatible polymeric material is silicone or other non-resorbable polymers known in the art. Examples of suitable materials of construction include poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, poly (siloxanes), copolymers thereof, and combinations thereof.

In an alternative embodiment, the biocompatible polymeric material is bioerodible. As used herein, the term "bioerodible" means that the material degrades in-vivo by dissolution, enzymatic hydrolysis, erosion, resorption, or a combination thereof. Examples of suitable bioerodible materials include synthetic polymers selected from poly(amides), poly(esters), poly(ester amides), poly(anhydrides), poly(orthoesters), polyphosphazenes, pseudo poly(amino acids), poly(glycerol-sebacate)(PGS), copolymers thereof, and mixtures thereof. In a preferred embodiment, the resorbable synthetic polymers are selected from poly(lactic acids), poly(glycolic acids), poly(lactic-co-glycolic acids), poly (caprolactones), and mixtures thereof. Other curable bioresorbable elastomers include poly(caprolactone) (PC) derivatives, amino alcohol-based poly(ester amides) (PEA) and poly (octane-diol citrate) (POC). PC-based polymers may require additional cross-linking agents such as lysine diisocyanate or 2,2-bis(8-caprolacton-4-yl)propane to obtain elastomeric properties.

In certain embodiments, the flexible elongate body defining the drug lumen is or includes a capillary tube or similar structure. The tube forming the drug lumen may be configured to have suitable wall strength and resistance to compression such that it resists collapse or constriction when deployed in the ureter.

As noted above, the bladder or first end portion and/or the kidney or second end portion of the elongate flexible body is/are biased in a curl/coil configuration in which the end portion is deformable between a retention shape and a deployment shape to facilitate insertion and placement of the device within a traditional ureteral stent or within the ureter of a patient using standard and conventional instruments, such as a guidewire and cystoscope. The term "retention shape" as used herein generally denotes any shape suited for retaining the drug delivery device or drug delivery device in the intended genitourinary location, and the term "deployment shape" as used herein generally denotes any shape suited for deploying/inserting the drug delivery device into a traditional ureteral catheter or for inserting the drug delivery device into the body through the working channel of catheter, cystoscope, or other deployment instrument positioned in the urethra.

As described above, the bladder, or first, end portion of the elongate flexible body may include a shape retention wire lumen in which a shape retention wire is disposed. Such a shape retention wire acts to bias the bladder or first end portion of the device into the retention shape. The shape retention wire may be formed of any elastic material effective to impart a suitable modulus or spring constant to the bladder end portion of the device. In a particular embodiment, the shape retention wire is an elastic wire formed from a superelastic alloy, such as nitinol. In another embodiment, the shape retention wire is formed of a biocompatible elastomer or other polymer. The shape retention wire may be formed from a shape-memory material, such as a shape memory alloy or polymer known in the art. For example, the wire may be formed of a low modulus elastomer, including but not limited to polyurethane, silicone, styrenic thermoplastic elastomer, and poly(glycerol-sebacate) (PGS).

In some embodiments, instead of or in addition to the shape retention wire, at least the bladder end portion of the elongate flexible body is formed of a shape-set polymer that is set to bias the bladder end portion in a retention shape. For example, the drug reservoir may be thermally shaped to have the retention shape. Thus, the drug reservoir may be formed of one or more thermoplastic materials that are suitable to be thermally formed into the retention shape. For example, the retention shape may be a curl or coil configuration. For example, suitable shape-set polymer materials may include thermoplastic silicone polyether polyurethane, aliphatic thermoplastic silicone polyether polyurethane, segmented polyether polyurethane, thermoplastic polyether polyurethane, thermoplastic polycarbonate polyurethane, other thermoplastic polyurethanes (TPUs), including aliphatic and aromatic, polycarbonate-based thermoplastic polyurethanes, and combinations or blends thereof.

In preferred embodiments, the bladder or first end portion of the device is configured to promote intravesical tolerability when in the retention shape. For example, the size and shape of the bladder or first end portion in combination with its pliability or compressibility (e.g., spring constant) preferably are selected to so that the bladder end portion is not so stiff and unpliable that it causes discomfort or pain to the patient when the bladder or first end portion of the device or drug delivery device contacts the bladder wall, which may occur during urination or contraction of the detrusor muscle. For example, U.S. Pat. No. 8,679,094 discloses that an intravesical device may be tolerable if compressible to a maximum dimension in any direction of about 3 cm with an acting force of about 1 N or less, such as an acting force of about 0.5 N, about 0.2 N, about 0.1 N, about 0.01 N, or less.

In certain embodiments, the bladder or first end portion, at least about the drug reservoir, has an outer diameter that is greater than the diameter of the flexible elongate body at the kidney or second end portion, as illustrated in FIGS. 1A, 4A, 5A, and 6A.

The flexible elongate body of the drug delivery device includes a drug lumen connecting the end portions of the device and serving as a conduit for the flow of drug from the bladder end portion to the kidney end portion. The drug lumen has a first end opening into the drug reservoir and a second end opening at the kidney end portion of the flexible elongate body.

In the drug delivery stent device, the drug lumen generally extends parallel with the drainage lumen, as illustrated in FIGS. 1A and 4A. In embodiments in which the flexible elongate body is a stent, the flexible body may include drainage holes in the sidewall, as shown in FIGS. 1A and 4A, or alternatively, such drainage holes may be omitted.

Figure 2:
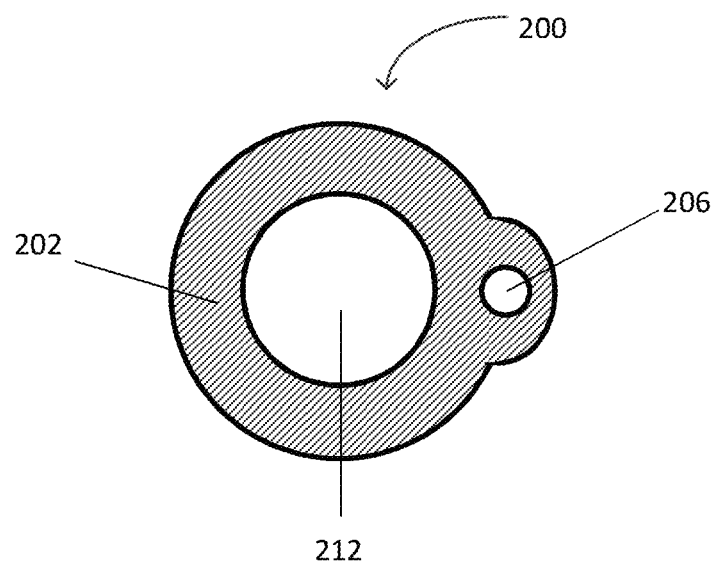
FIG. 2 is a cross-sectional view proximate to the kidney end portion of a drug delivery stent device in accordance with an embodiment of the present disclosure.

In embodiments, the drug lumen is generally defined in the flexible elongate body. In some embodiments, shown in FIGS. 1B and 4B, the drug lumen 104 and 304 are positioned within the flexible elongate body 102 and 302, respectively, proximate to the drainage lumen 112 and 312, respectively, in a configuration where the cross-sectional shapes of the sidewalls 122 and 322, respectively, are circular. The circular shape may facilitate ureteral insertion and operation of the ureteral stent and may be readily manufacturable by an extrusion process, for example. In another embodiment, shown in FIG. 2, drug delivery device 200 has a flexible elongate body 202 in which the drug lumen 206 is offset relatively further (as compared to the device in FIG. 1B) from the drainage lumen 212. The drug lumen may be defined by the same or different wall(s) as the drainage lumen.

Figure 3:
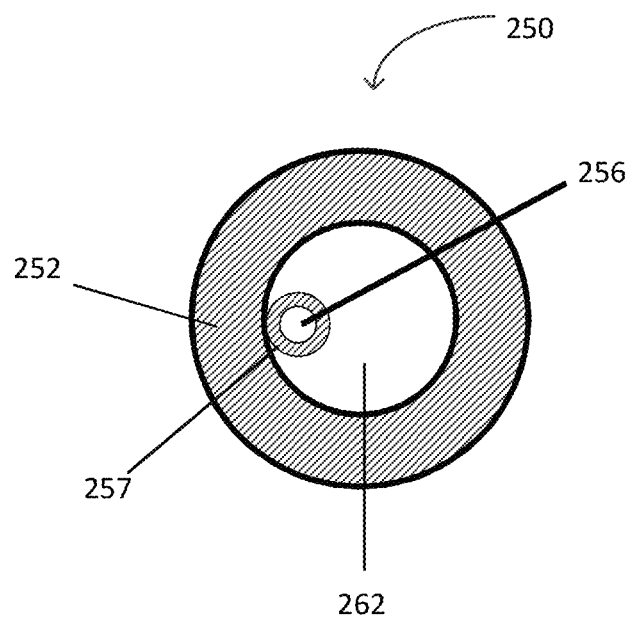
FIG. 3 is a cross-sectional view proximate to the kidney end portion of a drug delivery stent device in accordance with an embodiment of the present disclosure.

In another embodiment, as shown in FIG. 3, drug delivery device 250 has a flexible elongate body 252 defining drainage lumen 262, and drug lumen 256 is provided defined by a separate elongate body 257 disposed adjacent the flexible elongate body 252. For example, the drug lumen 256 may be disposed within or on the external surface of the flexible elongate body 252. These embodiments may provide additional wall thickness/structural support to the drug and drainage lumens, thereby increasing the mechanical integrity for the stent device.

Drug Reservoir and Semi-Permeable Wall

The drug reservoir is the space in which the drug is housed in the bladder, or first, end portion of the device. The drug reservoir is defined by (i.e., bounded by) one or more walls, at least one of part of which is formed of a semi-permeable material, which is effective to permit urine (or at least some of the water of the urine) in the bladder to permeate therethrough and enter the drug reservoir. The semi-permeable wall is semi-permeable in that, while it is permeable to water, it is substantially or completely impermeable to the drug in the reservoir and/or an excipient, so that solubilized drug and excipients cannot diffuse through the wall. In this way, water enters the drug reservoir, solubilizes the drug contained therein as well as the excipient (e.g., an osmotic excipient), creating an osmotic pressure in the drug reservoir. This pressure causes the solubilized drug to be pumped from the reservoir into and through the drug lumen, and out of the kidney, or second, end portion of the device.

The wall or walls defining the drug reservoir may be formed of any suitable material, and typically is formed of a biocompatible polymeric material. The wall or walls may be formed of a material that is the same as or different from the material forming the elongate flexible body of the device. The wall or walls defining the drug reservoir may be integral with the elongate flexible body, or the walls defining the drug reservoir may be formed as a separate structure that is then attached to the elongate flexible body. The flexible elongate body and walls defining the drug reservoir may be made, for example, by extrusion, molding, or a combination thereof.

In one embodiment of assembling the device prior to use, a specified quantity of a solid form of the drug is loaded into an opening in the drug reservoir (which may be in the bladder end of the device, for example) and then the opening is sealed with a mechanical plug or an adhesive substance, is closed off by a clamp mechanism, or is closed off by a combination of these means. In another embodiment, the opening is part of a reclosable valve suitable for receiving a needle for injecting a quantity of a semi-solid or liquid form of the drug.

Non-limiting examples of suitable materials of construction for the semi-permeable wall include silicones and polyurethanes known in the art.

In some embodiments, the device can include multiple drug reservoirs to deliver drug to the renal pelvis, in which each drug reservoir may contain the same drug or a different drug. In such embodiments, the device may further include a separate drug lumen for each drug reservoir. The drug from the additional drug reservoir may be osmotically pumped to the kidney end portion of the device in the renal pelvis, or alternatively, pumped directly into the bladder.

For example, the drug reservoir may be a flexible drug delivery device or include various features thereof, as described in U.S. Pat. Nos. 8,801,694, 8,182,464, and 8,343,516; U.S. Application Publications No. 2009/0149833, No. 2010/0003297, No. 2010/0331770, No. 2010/0060309, No. 2011/0202036, No. 2011/0152839, No. 2012/0089121, No. 2012/0089122, No. 2012/0203203, and No. 2016/000827; and PCT Publications No. WO2015/026813 and No. WO2015/069723. These publications are incorporated by reference herein, in pertinent part.

In some embodiments, the drug reservoir includes a flexible elongated housing. In such embodiments, the device may include a retention shape feature at the drug reservoir, to avoid having the flexible housing hanging flaccid from the drug lumen portion of the device and to impede collapse and voiding of the drug reservoir as the bladder contracts during urination. For example, as discussed herein, the retention shape may include a retention wire and/or a shape-set polymer that are biased in the desired retention shape. For example, the retention shape may include a coiled or "pretzel" shape. The pretzel shape essentially comprises at least two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the drug reservoir as a whole increases once the two sub-circles overlap.

In other embodiments, the drug reservoir may be small and/or rigid enough that the retention shape feature is not necessary. That is, the drug reservoir may be configured to hang freely from the drug lumen portion of the device. For example, in embodiments in which the amount of drug to be released is low (e.g., 5 mg/day for 7 days), the volume required for the drug reservoir is relatively small. In such embodiments, a shape retention feature may not be necessary, and the drug reservoir may be tubular with a circular, elliptical, annular, or rectangular cross-section and configured to connect to the opening of the drug lumen, without a retention wire or other retention feature.

In certain embodiments, as shown in FIG. 11, the drug reservoir 1104 is a closed device, which opens only at the point where the drug lumen 1106 enters the device. In this way, osmotic pressure drives water/urine in the bladder into the depot portion, where the drug is solubilized. Further osmotic behavior continues drawing water into the drug depot, at which point the drug solution can only escape through the drug lumen, traveling up the ureter until the exit which is located on the kidney end portion of the device. The drug then exits the device into the renal pelvis.

The Drug

The drug can be any suitable therapeutic, prophylactic, or diagnostic agent. The drug stored in and released from the device may consist only of the pharmaceutically active ingredient (API) or other agent of interest, or the drug may be formulated with one or more pharmaceutically acceptable excipients. The drug may be a biologic. The drug may be a metabolite. As used herein, the term "drug" with reference to any specific drug described herein includes its alternative forms, such as salt forms, free acid forms, free base forms, and hydrates. In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.001 mg/mL to about 10 mg/mL water at 37° C. The solubility of the drug may be affected at least in part by its form and dissolution medium pH. For example, a drug in the form of a water soluble salt may have a high solubility, while the same drug in base form may have a low solubility.

Specific and non-limiting examples of drugs that may be stored in and released from the present devices are described in the Methods of Treatment section below.

Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug. The excipient may facilitate loading of solid drug units into the drug reservoir of the device. For example, the excipients may increase the lubricity of the drug units so that the drug units can slide with reference to the interior lumen walls of the drug reservoir of the device. The excipient also may facilitate forming a therapeutic agent into a solid drug tablet that can be loaded into the drug reservoir. The excipients also may affect the kinetics of drug release from the device, such as by increasing or retarding the solubility or dissolution rate of the drug. In some embodiments, however, the drug release rate is predominately controlled by characteristics of the drug reservoir, such as the wall thickness and permeability to water or urine, while the excipient content of the drug units is primarily selected to permit reliable production of the drug, such as enabling the production of tablets or other solid units that are uniform, reproducible, and include a relatively high weight fraction of drug.

In some embodiments, the drug reservoir is similar to the drug delivery devices disclosed in PCT Publication No. WO2015/026813, and contains distinct tablets of drug and an excipient, which is a functional agent that facilitates release of the drug, such as an osmotic agent. In certain embodiments, the osmotic agent is lactose, urea, or another suitable agent.

In other embodiments, the drug reservoir contains a series of tablets having a similar formulation, such as a tablet containing both the active agent and an osmotic agent. For example, in such tablets the amount of drug may be from about 20 to about 30 percent.

The drug is to be released from the drug delivery device at a therapeutically effective rate. For some drugs, this may require the addition of one or more excipients, e.g., an osmotic agent to increase water flux, solubilizing or solubility enhancing agent, pH adjusting agent, or stability enhancing agent. Generally, the combination of the solubility of the selected drug in the presence or absence of functional agents, if any, and osmotic pressure flux will determine the release rate and duration, and such combination can be configured for the rate and duration to be within a therapeutically effective range. In embodiments where the drug is a low solubility drug, the drug may be formulated with an osmotic agent having a higher solubility than the drug, such that the osmotic agent expedites solubilization, causes osmotic pressure flux, and/or subsequent release of the drug. This beneficially allows for the delivery of low solubility or other drugs typically only delivered via diffusion, from osmotic delivery-based devices as described herein.

The drug can be loaded and stored in the devices in any suitable form. In a preferred embodiment, the drug is in a solid or semi-solid drug formulation in order to reduce the overall volume of the drug formulation and thereby reduce the size of the bladder end portion of the device, facilitating insertion through the patient's urethra and tolerability in bladder. The semi-solid form may be, for example, an emulsion or suspension; a gel or a paste. The solid form may be, for example, tablets, mini-tablets, pellets, beads, granules, or a powder. Non-limiting examples of suitable drug tablet forming methods are described in U.S. Application Publication No. 2010/0330149, which is incorporated herein by reference. In an alternative embodiment, the drug is loaded into the drug reservoir in a liquid form.

Advantageously, the drug is loaded into the reservoir of the drug delivery device prior to the device being inserted into the patient. That is, the drug reservoir does not need to be filled with a drug or a liquid vehicle after the device is inserted into the patient. This feature advantageously avoids subjecting the patient to additional or prolonged interventional steps during the procedure of deploying the device at its intended operational (bladder/ureter/renal pelvis) location within the patient, thereby minimizing risk of infection and patient discomfort.

In one embodiment, the drug units are shaped to align in a row when housed in the drug reservoir, such as the drug reservoir illustrated in FIGS. 4A and 6A. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug reservoir may be relatively flexible or deformable despite being loaded with a solid drug, as each drug unit may be permitted to move with reference to adjacent drug units.

Methods of Using the Drug Delivery Devices

In embodiments, the drug delivery devices described herein are used to administer one or more drugs to a patient in need thereof. As used herein, the term "patient" refers primarily to a human adult or child, but also may include other suitable mammalian animals, for example in a preclinical trial or in veterinary care. Advantageously, the methods enable the local, continuous delivery of the one or more drugs into the renal pelvis at therapeutically effective amounts over an extended period.

In one embodiment, the method includes first positioning or attaching the drug delivery device into or onto a ureteral stent and then inserting the drug delivery device and ureteral stent through the patient's urethra and bladder and into one of the patient's ureters, such that the bladder end portion of the device is located within the bladder of the patient and the kidney end portion of the device is located within a kidney of the patient; and then permitting water in the bladder to diffuse into a drug reservoir in the device through a semi-permeable wall of the device to create an osmotic pressure to pump the drug from the drug reservoir, through the drug lumen in the body of the device, out of the kidney end portion of the device, and into the renal pelvis. In other embodiments, the drug delivery device may be positioned within or adjacent the ureteral stent after deployment of the stent into the patient.

In one embodiment, the method includes inserting a drug delivery stent device (i.e., a device in which the flexible elongate body is a stent) through the patient's urethra and bladder and into one of the patient's ureters, such that the bladder end portion of the device is located within the bladder of the patient and the kidney end portion of the device is located within a kidney of the patient; and then permitting water in the bladder to diffuse into a drug reservoir in the device through a semi-permeable wall of the device to create an osmotic pressure to pump the drug from the drug reservoir, through a drug lumen in the body of the device, out of the device at the kidney end portion of the device, and into the renal pelvis.

In certain embodiments, the patient may have a reconstructed bladder, a neobladder, a stoma bag, or another means for collecting and storing urine. In such patients, the present devices may be utilized by deploying the device in the kidney and ureter, as described above, and locating the drug reservoir portion of the device at the site where urine is collected for the patient. Thus, the term "bladder" is not limited to anatomically intact bladders.

In some embodiments of the method, two drug delivery devices are used, with one device located in each ureter of the patient. In other embodiments of the method, only one device is used, located in the ureter corresponding to the right or left renal pelvis area in need of treatment. Advantageously, the methods do not require any kind of in vivo filling step, such as filling the drug reservoir of the device with the drug and/or with a liquid vehicle for the drug after the device is inserted into the patient.

In embodiments, the step of inserting the device into the patient includes passing the device through the patient's urethra and bladder and into a ureter using suitable deployment instruments under fluoroscopic guidance, cystoscopy guidance, or both. For example, the deployment instruments may include a cystoscope and a guidewire, which may be of a conventional design or a design specifically configured for insertion of the present devices. In one embodiment, the distal end of a guidewire is inserted through a lumen of a cystoscope, which is positioned in the urethra with a distal end of the cystoscope located in the bladder, and then the distal end of the guidewire is inserted into a ureter in the patient. The device is then passed through the cystoscope lumen over the guidewire and then positioned within the ureter, with or without the aid of a ureteral access sheath and/or a pusher. The guidewire typically extends through the drainage lumen of the device or an associated stent during this insertion step. After the device is positioned in the ureter, the guidewire is removed from the device, and accordingly removed from the ureter. Upon removal of the guidewire, the bladder end portion and/or the kidney end portion may coil or curve into a retention shape to keep the device positioned in the ureter. The coiled or curved retention shape may be the shape of the device in the absence of biasing force to maintain the device in a relatively straightened shape for insertion. For example, the retention shape may be set during manufacture of the device, such as by molding the polymeric material of which the body is formed. The retention shape alternatively or in addition may be imparted by a shape retention wire, such as a nitinol wire or other superelastic wire which is biased in a curl/coil configuration. In one embodiment, the device includes a shape retention wire lumen in the bladder end portion of the device, and the nitinol or superelastic wire is disposed in the shape retention wire lumen. After the device is inserted into the desired position, the cystoscope and/or other deployment instruments are withdrawn from the patient's bladder and urethra.

For example, as partially shown in FIG. 12, prior to an existing stent 1122 being threaded over the wireguide, the hood portion 1121 of the device 1100 device may be first threaded onto the wireguide, followed by the stent itself. The hood 1121 is mated over the leading end of the stent 1122 (like a glove), then a pusher may be used to push the stent 1122, and by extension, the hood portion 1121 of the device, into the renal pelvis 1111. The drug lumen 1106 and drug reservoir 1104 portions of the device, make their way through the urethra, following the stent 1122. Once the stent 1122 and hood portion 1121 are in place, the drug reservoir 1104 portion of the device 11000 is located in the bladder 1109, completing the placement of the device 1100, with the hood 1121 in the renal pelvis 1111, the drug reservoir 1104 in the bladder 1109, and the drug lumen 1106 connecting them through the ureter 1142. For example, an existing stent may have a coil at one or both of the bladder and renal ends.

Once the drug delivery device is positioned in ureter, the stent of the device (or an associated stent in embodiments in which the device itself does not include a stent) maintains patency of the ureteral lumen and facilitates the flow of urine from the kidney to the bladder, through a drainage lumen in the stent and/or around the outside of the stent body which is located in the ureteral lumen.

The water that diffuses through the semi-permeable wall and into the drug reservoir may be from urine in the bladder and in various embodiments, all, some or none of the other solutes/components in the urine may also diffuse through the wall. Water/urine in the bladder enters the drug reservoir of the drug delivery device through a semi-permeable wall. In one embodiment, the water/urine that enters the drug reservoir solubilizes a solid or semi-solid drug formulation that is housed in the drug reservoir. In an alternative embodiment, the drug is initially provided in the drug reservoir in a fluid form, such as a solution or suspension. The resulting drug solution cannot pass out of the reservoir through the semi-permeable wall, and therefore an osmotic pressure is generated. This pressure causes the drug solution to flow from the drug reservoir into, through a drug lumen in the device, and out of the device through a release aperture in the kidney end portion of the device. Thus the device effectively acts as an osmotic pump to pump the drug from the drug reservoir into the renal pelvis of the patient.

In embodiments, the device is configured to release a therapeutically or prophylactically effective amount of the drug over an extended period. In various embodiments, the drug is delivered to the patient over a period from one day to 90 days. In certain embodiments of the methods, the period is from 2 days to 80 days, from 3 days to 60 days, from 5 days to 45 days, from 7 days to the 30 days, from 3 days to 21 days, or from 3 days to 14 days. Other periods of drug release are envisioned. The amounts and rates of drug delivery will be selected, in part, depending upon the particular disease or condition being treated. In certain embodiments, the drug is released from the device at a zero order rate over a period from 1 day to 30 days, such as from 2 days to 21 days, or from 2 days to 14 days.

In certain embodiments, the device is configured to deliver drug to the tissue of a ureter in which the device is deployed. In such embodiments, the device may be configured such that a desired amount of drainage from the kidney travels along the outer surface of the stent/elongate body of the device, so that it contacts the tissue of the surrounding ureter. For example, the device may be configured such that the amount of drug delivered to the kidney is effective to generate a therapeutic concentration of drug in the urine being drained from the kidney to the bladder.

Following completion or substantial completion of drug release, or in certain circumstances earlier, the drug delivery device is removed from the patient. The step of removal may be carried by any suitable procedure. In one embodiment, the removal is carried out with the aid of a cystoscope or a urethral catheter and a grasping forceps passed through the cystoscope or catheter. Such instruments are known in the art. The device may include a retrieval string that may extend from the bladder end portion of the device and into the urethra. Such a retrieval string may extend out of the patient's urethra to facilitate device removal.

In one embodiment, the device is formed at least in part of a bioresorbable material, such that the device, or a part of the device, will biodegrade following drug release, thereby facilitating breakdown of the device, such that components of the device may be more easily removed from bladder and/or can be broken down into pieces small enough to be excreted with urine from the bladder.

Methods of Treatment with the Drug Delivery Devices

The deployed drug delivery device may release one or more drugs locally to the renal pelvis of a patient for local, regional, or systemic treatment or prophylaxis of a wide variety of diseases or conditions. Non-limiting examples include urinary tract infections, kidney infections (pyelonephritis), renal cell carcinoma, hyperfibrinolysis, upper tract urothelial carcinoma, and urinary stones, such as kidney stones, ureteral stones, and bladder stones. Treatments of other diseases and conditions are also envisioned.

In one embodiment, the patient is in need of treatment and/or prophylaxis of stones. Non-limiting examples of the drug to be delivered by the device include antimicrobials, alkalinizing agents, acidification agents, urease inhibitors, anti-inflammatories, and antifibrotics. In a particular embodiment, the drug delivery device is inserted into the patient following treating the patient with extracorporeal shock wave lithotripsy (ESWL) for treatment of kidney stones in the patient. The migration of smaller stone fragments to the lower part of the kidney or the lower pole calyces has been observed to occur post-ESWL treatment due to gravity and anatomical configuration (Bourdoumis, et al., "Lower Pole Stone Management" *Med Surg Urol* S1:002 (2012)). These stone fragments become relocated in the lower calyces and act as a nucleus for new stone formation leading to lower pole calyceal lithiasis. Accordingly, in embodiments of the present method, a drug that inhibits stone formation is released from the kidney end portion of the device, and also may become more concentrated and effective in these lower calyces due to gravity and anatomical configuration.

In one embodiment, the patient is in need of treatment or prophylaxis of a urinary tract infection (UTI) or pyelonephritis. In a particular embodiment, the method of treatment or prophylaxis includes delivering via the drug delivery device an antimicrobial agent. The antimicrobial agent may be an antibiotic, antibacterial, antifungal, antiviral, antiparasitic, disinfectant, or antiseptic agent known in the art. In certain embodiments, the antimicrobial may an aminoglycoside, a penem, or an iron mimetic. Non-limiting examples of specific antimicrobial agents that may be used in the methods of treatment or prophylaxis of UTI or pyelonephritis include trimethoprim/sulfamethoxazole, trimethoprim, ciprofloxacin, levofloxacin, norfloxacin, gatifloxacin, ofloxacin, nitrofurantoin, fosfomycin, pivmecillinam, cefpodoxime proxetil, ceftibuten, cefotaxime, ceftriaxone, ceftazidime, cefepime, amoxicillin/clavulanic acid, piperacillin/tazobactam, gentamicin, amikacin, ertapenem, imipenem/cilastatin, meropenem, doripenem, aztreonam, a gallium-based iron mimetic, and combinations thereof. In another embodiment, the "drug" administered to the patient includes an attenuated bacteria/pathogen for colonizing the genitourinary tract with a non-pathogenic bacteria to prevent recurrent urinary tract infection or pyelonephritis.

In another embodiment, the patient is in need of treatment of renal cell carcinoma. In particular embodiments, the method of treatment includes delivering via the drug delivery device an anti-angiogenesis agent, a tyrosine kinase inhibitor, an mTOR inhibitor, or a combination thereof. Non-limiting examples of specific drugs that may be used in the methods of treatment for renal cell carcinoma include everolimus, aldesleukin, bevacizumab, axitinib, sorafenib tosylate, pazopanib hydrochloride, aldesleukin, sunitnib malate, temsirolimus, and combinations thereof. Other treatments may be used in conjunction with the use of the device drug delivery devices described herein. For example, the method of treatment may further include surgery, for example a partial nephrectomy; radiation; or systemic chemotherapy.

In still another embodiment, the patient is in need of treatment of upper tract urothelial carcinoma, or transition cell cancer of the renal pelvis and ureter. Non-limiting examples of specific drugs that may be used in the methods of treatment for upper tract urothelial carcinoma include *Bacillus* Calmette-Guerin (BCG), mitomycin C, BCG/interferon, interferon (IFN)-2a, epirubicin, thiotepa, doxorubicin, gemcitabine, and combinations thereof. Other treatments may be used in conjunction with the use of the drug delivery devices described herein. For example, the method of treatment may further include surgery; radiation; or systemic chemotherapy.

In yet another embodiment, the patient is in need of treatment of hyperfibrinolysis. Non-limiting examples of specific drugs that may be used in the methods of treatment for hyperfibrinolysis include tranexamic acid, aminocaproic acid, and combinations thereof.

In still other embodiments, the methods of treatment may include releasing an anti-inflammatory agent, an antifibrotic agent, or a combination thereof, from the deployed drug delivery devices.

EXAMPLES

For examples 1-6, an experimental system was designed to simulate a ureteral drug delivery device having a flexible elongate body with a bladder end portion and a kidney end portion, a drug reservoir located at the bladder end portion which contains a drug and has a semi-permeable wall, and a drug lumen (capillary tube) having a first opening into the drug reservoir and a second end opening at the kidney end portion of the flexible elongate body. The ureteral drug delivery device used in the experiments was configured to permit water to enter the drug reservoir through the semi-permeable wall to create an osmotic pressure to pump the drug from the drug reservoir through the capillary tube and out of the device through the second end opening.

In each of these examples, the drug reservoir (a water-permeable silicone tube) was first filled with active tablets containing gemcitabine hydrochloride and osmotic tablets containing urea, which facilitate generation of an osmotic pressure in the drug reservoir and increase the solubility of the gemcitabine. An aggregate of osmotic tablets was placed serially next to that of active tablets, with the active tablets being adjacent the opening into the drug lumen. Each tablet had a diameter of 2.6 mm. The aggregated tablet lengths, when circular surface of each tablet was placed in contact with that of neighboring one, were approximately 11 and 4 cm for osmotic tablets and active tablets, respectively. The mass of the osmotic tablets was approximately 700 mg and that of active tablets was approximately 345 mg. Once the experimental system was made, the bladder end portion of the ureteral drug delivery device was submerged in a vial of degassed, deionized water, and the kidney end portion of the ureteral drug delivery device was connected to an High Performance Liquid Chromatography (HPLC) vial which was elevated above the drug reservoir by approximately 10 cm, to simulate the upward movement of the drug from the bladder through the ureter to the renal pelvis. The vials and ureteral drug delivery device were left in a chamber maintained at 37° C. to simulate the temperature conditions inside the body.

In each of the examples described below, periodic measurements of the weight of the HPLC vial containing the kidney end portion of the ureteral drug delivery device were taken to determine the volume of liquid in this vial, using the known density of the gemcitabine solution (approximately 1 g/mL) in a manner which will be apparent to those of skill in the art. Dilutions were made as necessary, and the concentration of gemcitabine was calculated using HPLC. These concentrations were used to determine the release rate of gemcitabine over time from the ureteral device, and the cumulative release of gemcitabine from the ureteral device.

The gauges of the polytetrafluoroethylene (PTFE) capillary tubing used to define the drug lumen and the dispensing needles used to connect the drug reservoir to the capillary tube were varied between experiments to test their ability to deliver gemcitabine from the kidney end portion of the ureteral drug delivery device, and to test their effect on the release of gemcitabine from the ureteral drug delivery device. An overview of these experimental conditions is provided in Table 1, below.

TABLE 1

Experimental Conditions for Examples 1-6

| Example | Capillary Tube Gauge | Capillary Tube Inner Diameter | Dispensing Needle Gauge | Dispensing Needle Inner Diameter | HPLC vial contents | Experiment Duration (Days) |
|---|---|---|---|---|---|---|
| 1 | 28 | 0.015 inches (0.38 mm) | 21 | 0.023 inches (0.58 mm) | empty | 14 |

TABLE 1-continued

Experimental Conditions for Examples 1-6

| Example | Capillary Tube Gauge | Capillary Tube Inner Diameter | Dispensing Needle Gauge | Dispensing Needle Inner Diameter | HPLC vial contents | Experiment Duration (Days) |
|---|---|---|---|---|---|---|
| 2 | 28 | 0.015 inches (0.38 mm) | 27 | 0.008 inches (0.20 mm) | water | 8 |
| 3 | 26 | 0.018 inches (0.46 mm) | 25 | 0.012 inches (0.30 mm) | water | 8 |
| 4 | 26 | 0.018 inches (0.46 mm) | 27 | 0.008 inches (0.20 mm) | water | 4 |
| 5 | 28 | 0.015 inches (0.38 mm) | 27 | 0.008 inches (0.20 mm) | empty | 4 |
| 6 | 28 | 0.015 inches (0.38 mm) | 27 | 0.008 inches (0.20 mm) | water | 4 |

Example 1

The ureteral drug delivery device described above was formed by connecting the drug reservoir to a 30 cm long 28 gauge PTFE capillary tube using a 21 gauge dispensing needle in the drug reservoir and luer lock. The kidney end portion of the ureteral drug delivery device was connected using a dispensing needle to an empty HPLC vial. The ureteral drug delivery device was left in this configuration for 14 days.

Figure 9:
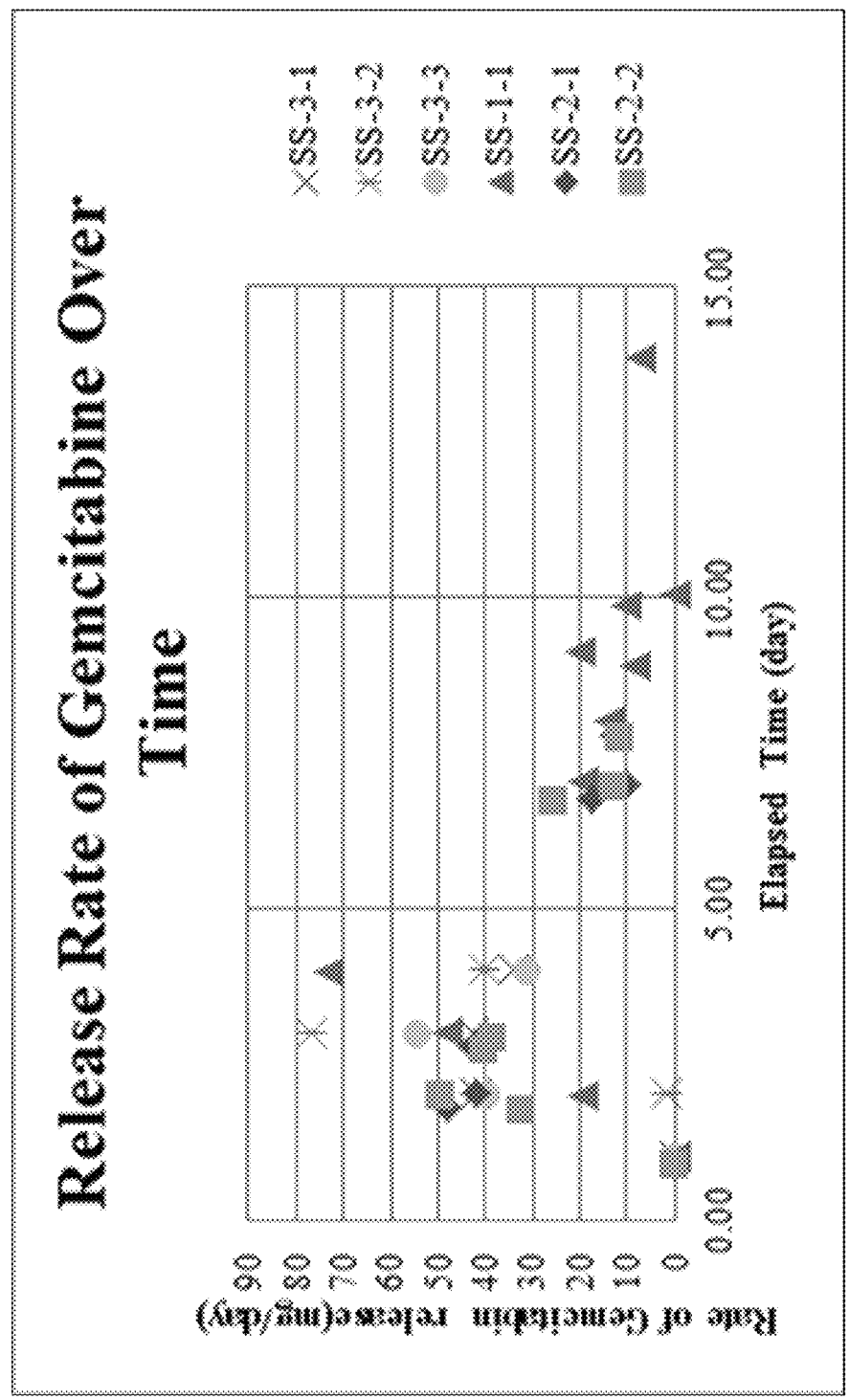
FIG. 9 is a graph plotting the release rate of gemcitabine over time from six different experimental systems using a drug delivery device in accordance with an embodiment of the present disclosure.
Figure 10:
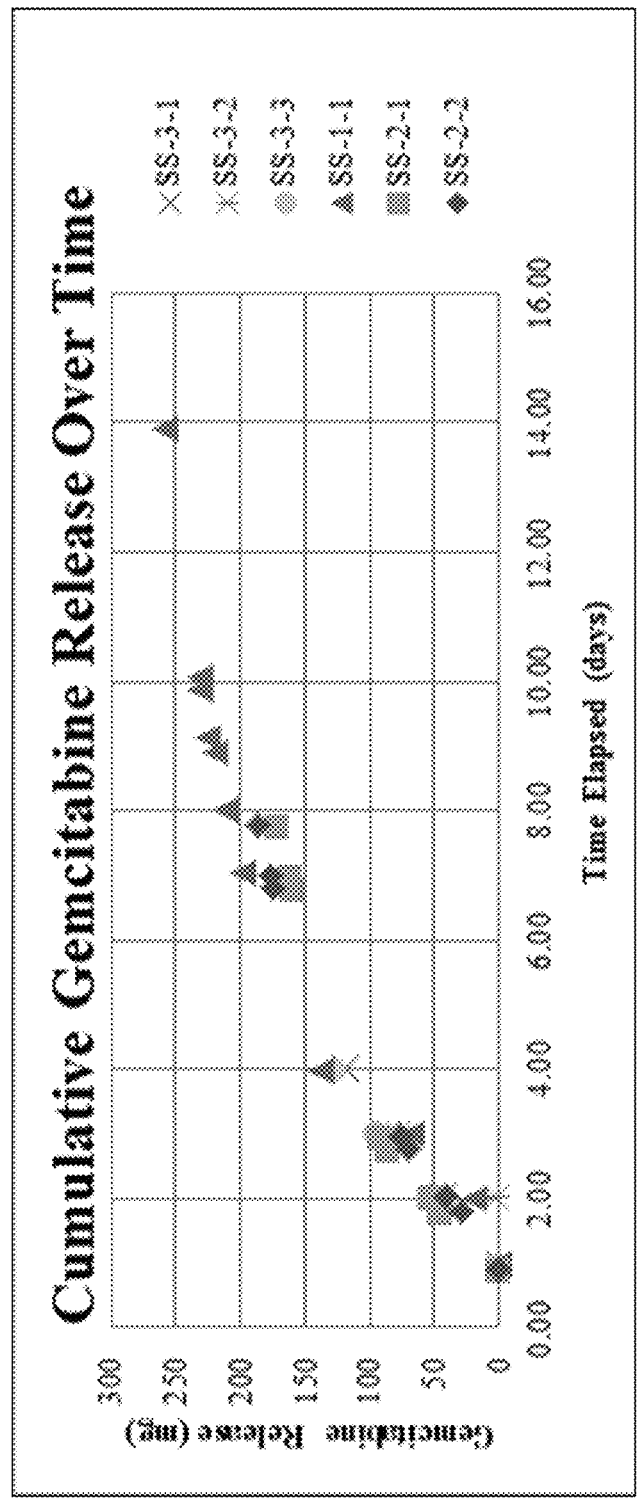
FIG. 10 is a graph plotting the cumulative release of gemcitabine over time from six different experimental systems using a drug delivery device in accordance with an embodiment of the present disclosure.

The release rate of gemcitabine over time from the ureteral drug delivery device described in this example is shown in points labeled SS-1-1 in FIG. 9. The cumulative release of gemcitabine over time from the ureteral device described in this example is shown in points labeled SS-1-1 in FIG. 10. FIGS. 9 and 10 show that this device is effective in delivering gemcitabine through the kidney end portion of the device.

As shown in FIG. 9, a biphasic release rate profile was observed for this example, with a lag time from the time the device was inserted into the vials until the device began to release gemcitabine at the kidney end portion, followed by a sharp increase in the first phase, after which the release rate steadily drops over time. As shown in FIG. 10, compared to other examples in which the HPLC vial contained water, this example exhibits a relatively long lag time, taking longer to deliver the same amount of gemcitabine from the kidney end portion as other examples, but eventually releases a higher total amount of gemcitabine.

Example 2

The ureteral drug delivery device described above was formed by connecting the drug reservoir to a 30 cm long 28 gauge PTFE capillary tube using the steel portion of a 27 gauge dispensing needle. The kidney end portion of the ureteral drug delivery device was connected to an HPLC vial which contained water. The kidney end portion of the ureteral drug delivery device was connected to the HPLC vial without the use of a dispensing needle. The ureteral drug delivery device was left in this configuration for 8 days.

The release rate of gemcitabine over time from the ureteral device described in this example is shown in points labeled SS-2-1 in FIG. 9. The cumulative release of gemcitabine over time from the ureteral device described in this example is shown in points labeled SS-2-1 in FIG. 10. FIGS. 9 and 10 show that this device is effective in delivering gemcitabine through the kidney end portion of the ureteral drug delivery device.

As shown in FIG. 9, a biphasic release rate profile for this example, with a lag time from the time the device was inserted into the vials until the device began to release gemcitabine at the kidney end portion, followed by a sharp increase in the first phase, after which the release rate steadily drops over time. As shown in FIG. 10, compared to other examples in which the HPLC vial did not contain water, this example exhibits a relatively short lag time, taking less time to deliver the same amount of gemcitabine from the kidney end portion as other examples. However, compared to other examples in which the HPLC vial did not contain water, this example eventually releases a lower total amount of gemcitabine.

Example 3

The ureteral drug delivery device described above was formed by connecting the drug reservoir to a 30 cm long 26 gauge PTFE capillary tube using the steel portion of a 25 gauge dispensing needle. The kidney end portion of the ureteral drug delivery device was connected to an HPLC vial which contained water. The kidney end portion of the ureteral device was connected to the HPLC vial without the use of a dispensing needle. The ureteral drug delivery device was left in this configuration for 8 days.

The release rate of gemcitabine over time from the ureteral device described in this example is shown in points labeled SS-2-2 in FIG. 9. The cumulative release of gemcitabine over time from the ureteral device described in this example is shown in points labeled SS-2-2 in FIG. 10. FIGS. 9 and 10 show that this device is effective in delivering gemcitabine through the kidney end portion of the ureteral stent device.

As shown in FIG. 9, a biphasic release rate profile was observed for this example, with a lag time from the time the device was inserted into the vials until the device began to release gemcitabine at the kidney end portion, followed by a sharp increase in the first phase, after which the release rate steadily drops over time. As shown in FIG. 10, compared to other examples in which the HPLC vial did not contain water, this example exhibits a relatively short lag time, taking less time to deliver the same amount of gemcitabine from the kidney end portion as other examples. However, compared to other examples in which the HPLC vial did not contain water, this example eventually releases a lower total amount of gemcitabine.

Example 4

The ureteral stent described above was formed by connecting the drug reservoir to a 30 cm long 26 gauge PTFE capillary tube using the steel portion of a 27 gauge dispensing needle. The kidney end portion of the ureteral stent device was connected to an HPLC vial which contained water. The kidney end portion of the ureteral stent was connected to the HPLC vial without the use of a dispensing needle. The ureteral stent device was left in this configuration for 4 days.

The release rate of gemcitabine over time from the ureteral device described in this example is shown in points labeled SS-3-1 in FIG. 9. The cumulative release of gemcitabine over time from the ureteral device described in this example is shown in points labeled SS-3-1 in FIG. 10. FIGS. 9 and 10 show that this device is effective in delivering gemcitabine through the kidney end portion of the ureteral stent device.

As shown in FIG. 9, a biphasic release rate profile was observed for this example, with a lag time from the time the device was inserted into the vials until the device began to release gemcitabine at the kidney end portion, followed by a sharp increase in the first phase, after which the release rate steadily drops over time. As shown in FIG. 10, compared to other examples in which the HPLC vial did not contain water, this example exhibits a relatively short lag time, taking less time to deliver the same amount of gemcitabine from the kidney end portion as other examples. However, compared to other examples in which the HPLC vial did not contain water, this example eventually releases a lower total amount of gemcitabine.

Example 5

The ureteral drug delivery device described above was formed by connecting the drug reservoir to a 30 cm long 28 gauge PTFE capillary tube using the steel portion of a 27 gauge dispensing needle. The kidney end portion of the ureteral stent device was connected to an empty HPLC vial. The kidney end portion of the ureteral stent was connected to the HPLC vial without the use of a dispensing needle. The ureteral stent device was left in this configuration for 4 days.

The release rate of gemcitabine over time from the ureteral device described in this example is shown in points labeled SS-3-2 in FIG. 9. The cumulative release of gemcitabine over time from the ureteral device described in this example is shown in points labeled SS-3-2 in FIG. 10. FIGS. 9 and 10 show that this device is effective in delivering gemcitabine through the kidney end portion of the ureteral stent device.

As shown in FIG. 9, a biphasic release rate profile was observed for this example, with a lag time from the time the device was inserted into the vials until the device began to release gemcitabine at the kidney end portion, followed by a sharp increase in the first phase, after which the release rate steadily drops over time. As shown in FIG. 10, compared to other examples in which the HPLC vial contained water, this example exhibits a relatively long lag time, taking longer to deliver the same amount of gemcitabine from the kidney end portion as other examples, but eventually releases a higher total amount of gemcitabine.

Example 6

The ureteral drug delivery device described above was formed by connecting the drug reservoir to a 30 cm long 28 gauge PTFE capillary tube using the steel portion of a 27 gauge dispensing needle. The kidney end portion of the ureteral drug delivery device was connected to an HPLC vial which contained water. The kidney end portion of the ureteral device was connected to the HPLC vial without the use of a dispensing needle. The ureteral drug delivery device was left in this configuration for 4 days.

The release rate of gemcitabine over time from the ureteral device described in this example is shown in points labeled SS-3-3 in FIG. 9. The cumulative release of gemcitabine over time from the ureteral device described in this example is shown in points labeled SS-3-3 in FIG. 10. FIGS. 9 and 10 show that this device is effective in delivering gemcitabine through the kidney end portion of the ureteral stent device.

As shown in FIG. 9, a biphasic release rate profile was observed for this example, with a lag time from the time the device was inserted into the vials until the device began to release gemcitabine at the kidney end portion, followed by a sharp increase in the first phase, after which the release rate steadily drops over time. As shown in FIG. 10, compared to other examples in which the HPLC vial did not contain water, this example exhibits a relatively short lag time, taking less time to deliver the same amount of gemcitabine from the kidney end portion as other examples. However, compared to other examples in which the HPLC vial did not contain water, this example eventually releases a lower total amount of gemcitabine.

Overall, the basic release rate profile for each of the six systems was substantially the same. Release rate over time showed a biphasic release profile. There was a lag time, followed by a sharp increase in the first phase, after which the release rate steadily dropped over time. Additionally, the cumulative release profile, after the lag time, appeared to be a steady logarithmic curve across all six systems.

As shown in FIG. 9, all six systems showed almost no delivery of gemcitabine in the first day. But after that, a more drastic variation among the six systems was seen on the second day. This showed that the lag time associated with each of the systems varied. It appeared that systems without water added to the vials beforehand (SS-1-1, SS-3-2) had a longer lag time compared to those systems that had water. In other words, they took longer to deliver the same amounts of gemcitabine as the other systems. However, the systems without water delivered gemcitabine at a faster rate during their peak (~74 mg/day), than those with water (~50 mg/day). Since the systems without water had a longer lag time and a higher peak delivery rate compared to the systems with water, it is possible that the presence of water makes the release profile smoother. It is also suspected that the reduction in the dead volume contributes to the decreased lag time experienced between SS-1-1 and the other systems. It also appears that tubing size has a very small, if not negligible, effect on the release rates.

Looking at FIG. 10, the systems with a greater lag time (SS-1-1, SS-3-2) delivered the least amount of gemcitabine in the first few days, consistent with the observation that they had a longer lag time, which was derived from FIG. 9. However, over time, the systems with a greater lag time delivered more gemcitabine than those with less lag time. It is postulated that this phenomenon arises from the fact that the systems with less of a lag time initially deliver drug more quickly than the others. However, the osmotic pressure that drove the delivery of gemcitabine was dependent on how much osmotic agent remained in the device. Since the device with less lag time delivered more fluid initially, the osmotic agent in those devices was depleted more quickly. However, in those systems with greater lag time, the osmotic agent was not depleted as rapidly. Therefore, while the systems with more lag time may deliver more drug in the short term, over the long term, the delivery rate of those systems decreases lower than the rate of the systems, which more initial lag time, since those systems have more osmotic agent left.

Thus, these systems demonstrate that it is indeed possible to drive a fluid upwards through a capillary tube towards a delivery site. The basis for a device to deliver drug from the bladder, through the ureter, to the renal pelvis was shown to be feasible in vitro. A biphasic profile was shown for release rate per day of gemcitabine and a logarithmic profile was shown for cumulative release. It was postulated that a reduction in the dead volume of the system correlates to a reduced lag time in the delivery. It was further noted that the presence of water in the delivery site smoothed the graph of the release rate per day, reducing the lag time, as well as the peak rate of delivery. Systems with more lag time were observed to delivery less gemcitabine in the short term, but more gemcitabine in the long term.

Example 7

Another experimental system was designed to simulate a ureteral drug delivery device having a flexible elongate body with a bladder end portion and a kidney end portion, a drug reservoir located at the bladder end portion which contains a drug and has a semi-permeable wall, and a drug lumen (capillary tube) having a first opening into the drug reservoir and a second end opening at the kidney end portion of the flexible elongate body. The ureteral drug delivery device used in the experiments was configured to permit water to enter the drug reservoir through the semi-permeable wall to create an osmotic pressure to pump the drug from the drug reservoir through the capillary tube and out of the device through the second end opening.

In this experiment, a drug reservoir similar to that illustrated in FIG. 11A was prepared. In particular, a spacer end piece was adhered using silicone adhesive within a tubular silicone housing. 10.5 cm of urea tablets, 4 cm of lactose tablets, and one tablet containing methylene blue were loaded into the tubular housing. A capillary tube (36 cm) having two spacers disposed in a spaced relationship at one end was slid into the tubular housing of the drug reservoir, adjacent the methylene blue tablet. Silicone adhesive was applied in the space between the spacers with a needle inserted between the spacer and the drug reservoir tube, to secure the spacers, capillary tube, and drug reservoir tube. Thus, the drug reservoir contained no opening or orifice, other than the capillary tube.

The drug reservoir was submerged in 125 mL of degassed, deionized water and the capillary tube was extended vertically and secured. The open end of the capillary tube was inserted into a sealed vial containing 13.5 mL degassed, deionized water, to simulate the upward movement of the drug from the bladder through the ureter to the renal pelvis. Movement of the methylene blue up the capillary tube was observed, demonstrating the ability of osmotic pressure within the drug reservoir to drive water/urine in the bladder into the drug reservoir portion, where the drug is solubilized. Further osmotic behavior continues drawing water into the drug depot, at which point the drug solution can only escape through the capillary tube, traveling up the ureter until the exit which is located on the kidney end portion of the device.

Modifications and variations of the devices and methods described herein will be obvious to those skilled in the art from the foregoing detailed description. Such modifications and variations are intended to come within the scope of the appended claims.

We claim:

1. A method of administering a drug to a patient in need thereof, comprising:
   inserting a drug delivery device comprising a flexible elongate body having a bladder end portion, a kidney end portion, and a drug lumen extending between the bladder end portion and the kidney end portion, through the patient's urethra and bladder and into at least one of the patient's ureters, such that the bladder end portion of the device is located within the bladder of the patient and the kidney end portion of the device is located within a kidney of the patient, wherein the bladder end portion comprises a drug reservoir that is defined at least in part by a semi-permeable wall and contains a drug; and
   permitting water in the bladder to diffuse through the semi-permeable wall of the device to create an osmotic pressure within the drug reservoir to pump the drug from the bladder end portion through the drug lumen and out of the device through an opening at the kidney end portion of the device and into the renal pelvis.

2. The method of claim 1, wherein the drug is released into the renal pelvis continuously over a treatment period from one day to 90 days.

3. The method of claim 1, which does not include a step of manually filling the drug reservoir of the device with a liquid after the device is inserted into the patient.

4. The method of claim 1, wherein inserting the drug delivery device comprises positioning the drug delivery device within or adjacent a ureteral stent.

5. The method of claim 1, wherein the flexible elongate body is a ureteral stent and further comprises a drainage lumen extending between the bladder end portion and the kidney end portion.

6. The method of claim 1, wherein the drug delivery device is inserted following treating the patient with extracorporeal shock wave lithotripsy for treatment of kidney stones in the patient.

7. The method of claim 1, wherein the patient is in need of treatment or prophylaxis of a urinary tract infection or pyelonephritis.

8. The method of claim 7, wherein the drug comprises an antimicrobial agent.

9. The method of claim 7, wherein the drug comprises an aminoglycoside, a penem, or an iron mimetic.

10. The method of claim 7, wherein the drug comprises an antibiotic agent, an antibacterial agent, an antifungal agent, an antiviral agent, an antiparasitic agent, a disinfectant agent, or an antiseptic agent.

11. The method of claim 7, wherein the drug is selected from the group consisting of trimethoprim/sulfamethoxazole, trimethoprim, ciprofloxacin, levofloxacin, norfloxacin, gatifloxacin, ofloxacin, nitrofurantoin, fosfomycin, pivmecillinam, cefpodoxime proxetil, ceftibuten, cefotaxime, ceftriaxone, ceftazidime, cefepime, amoxicillin/clavulanic acid, piperacillin/tazobactam, gentamicin, amikacin, ertapenem, imipenem/cilastatin, meropenem, doripenem, aztreonam, a gallium-based iron mimetic, and combinations thereof.

12. The method of claim 7, wherein the drug comprises attenuated bacteria/pathogen for colonizing the genitourinary tract with non-pathogenic bacteria to prevent recurrent urinary tract infection or pyelonephritis.

13. The method of claim 1, wherein the patient is in need of treatment of renal cell carcinoma.

14. The method of claim 13, wherein the drug is selected from the group consisting of everolimus, aldesleukin, bevacizumab, axitinib, sorafenib tosylate, pazopanib hydrochloride, aldesleukin, sunitnib malate, temsirolimus, and combinations thereof.

15. The method of claim 1, wherein the patient is in need of treatment of upper tract urothelial carcinoma.

16. The method of claim 15, wherein the drug is selected from the group consisting of *Bacillus Calmette-Guerin* (BCG), Mitomycin C, BCG/interferon, interferon-2a, epirubicin, doxorubicin, thiotepa, gemcitabine, and combinations thereof.

17. The method of claim 1, wherein the patient is in need of treatment of hyperfibrinolysis.

18. The method of claim 17, wherein the drug is selected from the group consisting of tranexamic acid, aminocaproic acid, and combinations thereof.

19. The method of claim 1, wherein the patient is in need of treatment of urinary stones.

20. The method of claim 19, wherein the drug is selected from the group consisting of antimicrobials, alkalinizing agents, acidification agents, urease inhibitors, and combinations thereof.

21. The method of claim 1, wherein the drug comprises an anti-inflammatory agent or an antifibrotic agent.

22. A method of administering a drug to a patient in need thereof, comprising:
    inserting a drug delivery device comprising a flexible elongate body having a bladder end portion, a kidney end portion, and a drug lumen extending between the bladder end portion and the kidney end portion, through the patient's urethra and bladder and into at least one of the patient's ureters, such that the bladder end portion of the device is located within the bladder of the patient and the kidney end portion of the device is located within a kidney of the patient, wherein the bladder end portion comprises a drug reservoir, which is separate from and in fluid communication with the drug lumen, and that is defined at least in part by a semi-permeable wall and contains a drug; and
    permitting water in the bladder to diffuse through the semi-permeable wall of the device to create an osmotic pressure to pump the drug from the bladder end portion through the drug lumen and out of the device through an opening at the kidney end portion of the device and into the renal pelvis.

23. The method of claim 22, wherein the drug is released into the renal pelvis continuously over a treatment period from one day to 90 days.

24. The method of claim 22, which does not include a step of manually filling the drug reservoir of the device with a liquid after the device is inserted into the patient.

25. The method of claim 22, wherein inserting the drug delivery device comprises positioning the drug delivery device within or adjacent a ureteral stent.

26. The method of claim 22, wherein the flexible elongate body is a ureteral stent and further comprises a drainage lumen extending between the bladder end portion and the kidney end portion.

27. The method of claim 22, wherein the drug comprises an anti-inflammatory agent or an antifibrotic agent.

28. The method of claim 22, wherein the drug delivery device is inserted following treating the patient with extracorporeal shock wave lithotripsy for treatment of kidney stones in the patient.

29. The method of claim 22, wherein the patient is in need of treatment or prophylaxis of a urinary tract infection or pyelonephritis.

30. The method of claim 22, wherein the patient is in need of treatment of renal cell carcinoma or upper tract urothelial carcinoma.

* * * * *